(12) United States Patent
Leeflang et al.

(10) Patent No.: US 8,758,847 B2
(45) Date of Patent: Jun. 24, 2014

(54) APPARATUS AND METHODS FOR MAKING COATED LINERS AND TUBULAR DEVICES INCLUDING SUCH LINERS

(75) Inventors: Stephen Arie Leeflang, Sunnyvale, CA (US); Christian Scott Eversull, Palo Alto, CA (US)

(73) Assignee: Aust Development, LLC, Mountain View, CA (US)

( * ) Notice: Subject to any disclaimer, the term of this patent is extended or adjusted under 35 U.S.C. 154(b) by 1307 days.

(21) Appl. No.: 12/551,545

(22) Filed: Aug. 31, 2009

(65) Prior Publication Data

US 2010/0211047 A1    Aug. 19, 2010

Related U.S. Application Data

(60) Provisional application No. 61/153,295, filed on Feb. 18, 2009, provisional application No. 61/223,352, filed on Jul. 6, 2009, provisional application No. 61/227,745, filed on Jul. 22, 2009, provisional application No. 61/234,311, filed on Aug. 16, 2009.

(51) Int. Cl.
*B29C 53/36* (2006.01)
*A61M 25/00* (2006.01)
*B05B 3/12* (2006.01)
*B05B 1/02* (2006.01)

(52) U.S. Cl.
USPC ...... 427/2.28; 427/2.1; 427/424; 156/244.18; 156/203; 156/217; 156/218; 604/265; 604/523

(58) Field of Classification Search
USPC ............ 156/277, 278, 203, 216–218; 604/19, 604/523, 265; 427/424, 2.1, 2.24, 2.25, 427/2.28

See application file for complete search history.

(56) References Cited

U.S. PATENT DOCUMENTS

| | | | |
|---|---|---|---|
| 2,805,973 A | 9/1957 | Klasing et al. | |
| 3,269,278 A | 8/1966 | Olstad | |
| 3,511,435 A | 5/1970 | Cawley et al. | |
| 3,540,959 A | 11/1970 | Houghton | |

(Continued)

FOREIGN PATENT DOCUMENTS

| WO | 9113648 | 9/1991 |
|---|---|---|
| WO | WO 9113648 A * | 9/1991 |

(Continued)

OTHER PUBLICATIONS

International Publication No. WO 99/01281; Applicant: Thermon Manufacturing Company; 20 pages, Jul. 29, 1999.

(Continued)

*Primary Examiner* — Cachet Sellman
(74) *Attorney, Agent, or Firm* — William A. English; Vista IP Law Group LLP

(57) ABSTRACT

A medical device includes a proximal end, a distal end sized for introduction into a body lumen, and a lumen extending between the proximal and distal ends. The tubular device includes an inner liner including a coating on an inner surface thereof, a reinforcing layer surrounding at least a portion of the liner; and an outer layer surrounding the reinforcing layer and inner liner. The liner and outer layer may include multiple sections having different properties than one another, adjacent sections attached together by seams, which may be offset from one another. Apparatus and methods for making tubular devices with coated liners are also provided.

16 Claims, 15 Drawing Sheets

(56) References Cited

U.S. PATENT DOCUMENTS

| | | | |
|---|---|---|---|
| 3,879,516 A | 4/1975 | Wolvek | |
| 4,478,898 A | 10/1984 | Kato | |
| 4,516,972 A | 5/1985 | Samson | |
| 4,636,346 A | 1/1987 | Gold et al. | |
| 4,863,442 A | 9/1989 | DeMello et al. | |
| 4,955,899 A * | 9/1990 | Della Corna et al. | 623/1.46 |
| 5,047,045 A | 9/1991 | Arney et al. | |
| 5,176,661 A | 1/1993 | Evard et al. | |
| 5,217,440 A | 6/1993 | Frassica | |
| 5,254,107 A | 10/1993 | Soltesz | |
| 5,370,655 A | 12/1994 | Burns | |
| 5,400,785 A | 3/1995 | Crowley | |
| 5,447,497 A | 9/1995 | Sogard et al. | |
| 5,514,236 A | 5/1996 | Avellanet et al. | |
| 5,549,109 A | 8/1996 | Samson et al. | |
| 5,569,221 A | 10/1996 | Houser et al. | |
| 5,676,659 A | 10/1997 | McGurk | |
| 5,713,867 A | 2/1998 | Morris | |
| 5,735,809 A | 4/1998 | Gorsuch | |
| 5,811,043 A | 9/1998 | Horrigan et al. | |
| 5,836,926 A | 11/1998 | Peterson et al. | |
| 5,967,988 A | 10/1999 | Briscoe et al. | |
| 6,004,310 A | 12/1999 | Bardsley et al. | |
| 6,027,779 A | 2/2000 | Campbell et al. | |
| 6,177,523 B1 | 1/2001 | Reich et al. | |
| 6,183,443 B1 | 2/2001 | Kratoska et al. | |
| 6,217,566 B1 | 4/2001 | Ju et al. | |
| 6,293,907 B1 | 9/2001 | Axon et al. | |
| 6,310,244 B1 | 10/2001 | Tran et al. | |
| 6,315,792 B1 | 11/2001 | Armstrong et al. | |
| 6,511,462 B1 | 1/2003 | Itou et al. | |
| 6,592,576 B2 | 7/2003 | Andrews et al. | |
| 6,669,886 B1 | 12/2003 | Willard | |
| 6,830,568 B1 | 12/2004 | Kesten et al. | |
| 6,837,890 B1 | 1/2005 | Chludzinski et al. | |
| 6,942,654 B1 | 9/2005 | Schaefer et al. | |
| 6,945,970 B2 | 9/2005 | Pepin | |
| 6,946,173 B2 | 9/2005 | Lim et al. | |
| 6,979,290 B2 | 12/2005 | Mourlas | |
| 7,188,623 B2 | 3/2007 | Andreson et al. | |
| 7,273,469 B1 | 9/2007 | Chan et al. | |
| 7,306,585 B2 | 12/2007 | Ross | |
| 7,504,125 B1 * | 3/2009 | Pacetti et al. | 427/2.24 |
| 7,520,950 B2 | 4/2009 | Saadat et al. | |
| 7,550,053 B2 | 6/2009 | Leeflang et al. | |
| 7,553,387 B2 | 6/2009 | Leeflang et al. | |
| 2001/0016702 A1 | 8/2001 | Benjamin | |
| 2001/0053931 A1 | 12/2001 | Hess et al. | |
| 2002/0156494 A1 | 10/2002 | Simhambhatia et al. | |
| 2003/0233115 A1 | 12/2003 | Eversull et al. | |
| 2005/0059957 A1 | 3/2005 | Campbell et al. | |
| 2005/0085841 A1 | 4/2005 | Eversull et al. | |
| 2005/0085842 A1 | 4/2005 | Eversull et al. | |
| 2005/0149104 A1 | 7/2005 | Leeflang et al. | |
| 2005/0197623 A1 | 9/2005 | Leeflang et al. | |
| 2005/0228452 A1 | 10/2005 | Mourlas et al. | |
| 2006/0005841 A1 | 1/2006 | Anderson | |
| 2007/0074805 A1 | 4/2007 | Leeflang et al. | |
| 2007/0075452 A1 | 4/2007 | Leeflang et al. | |
| 2007/0088296 A1 | 4/2007 | Leeflang et al. | |
| 2007/0169877 A1 * | 7/2007 | Leeflang et al. | 156/218 |
| 2007/0270779 A1 * | 11/2007 | Jacobs et al. | 604/525 |
| 2009/0126862 A1 | 5/2009 | Leeflang et al. | |
| 2009/0227962 A1 | 9/2009 | Eversull et al. | |

FOREIGN PATENT DOCUMENTS

| | | |
|---|---|---|
| WO | 9620750 | 7/1996 |
| WO | 9740880 | 11/1997 |
| WO | 9851370 | 11/1998 |
| WO | 9937350 | 7/1999 |
| WO | 0107101 | 2/2001 |
| WO | 03020353 | 3/2003 |
| WO | 2004075961 | 9/2004 |

OTHER PUBLICATIONS

European Supplemental Search Report and Written Opinion for corresponding Application EP 10 74 4320, Applicant: AUST Development, LLC, EPO Form 1703, 1503 and P0459; dated Jul. 31, 2012, 6 pages.

* cited by examiner

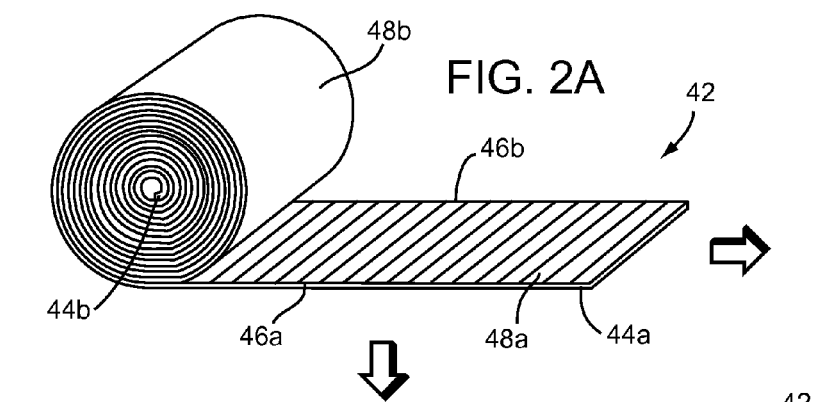
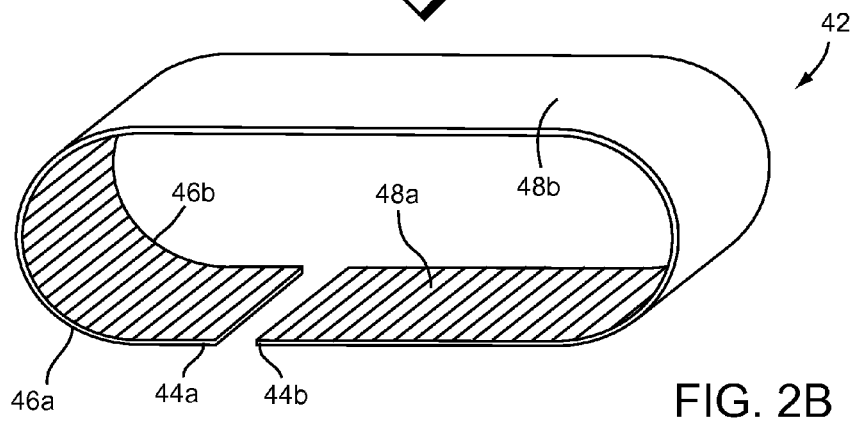
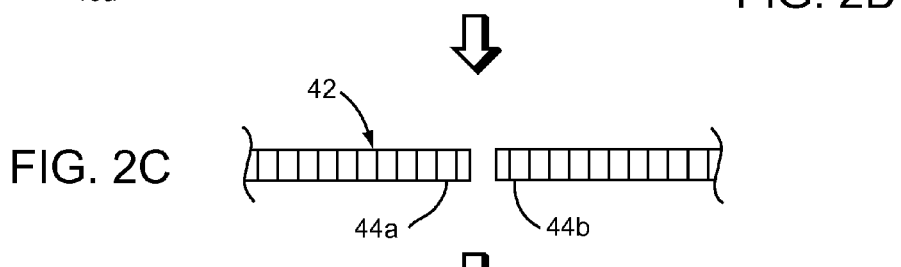
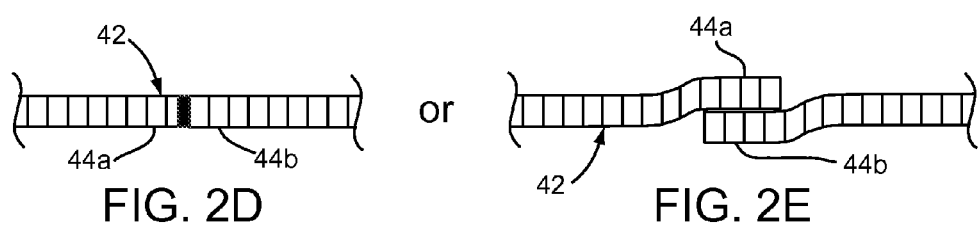

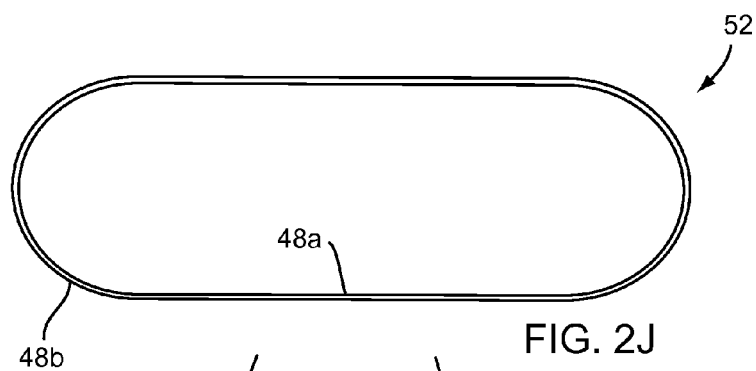
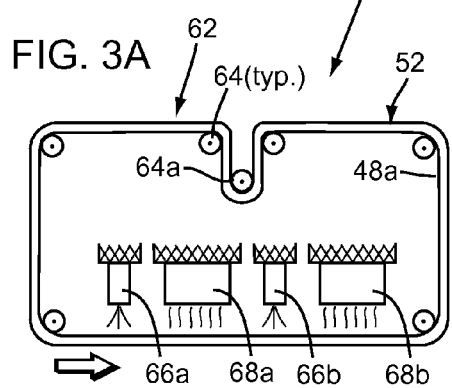
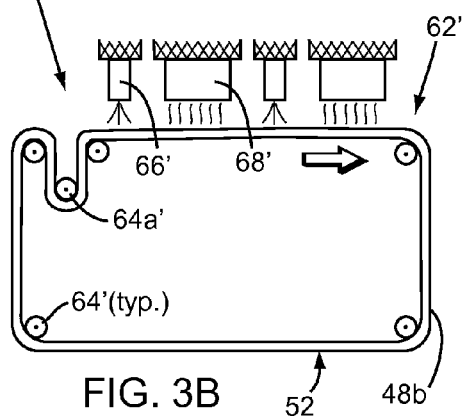
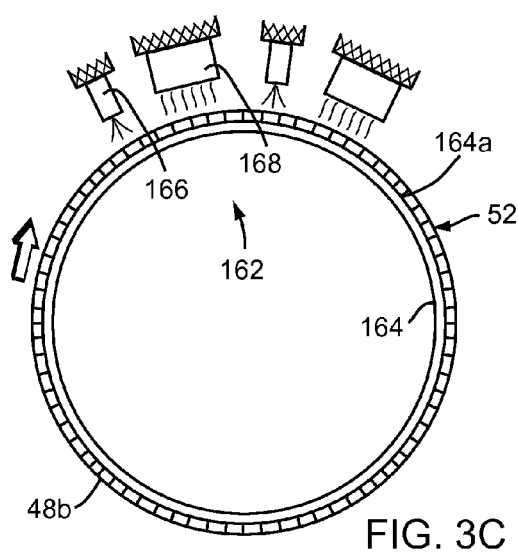
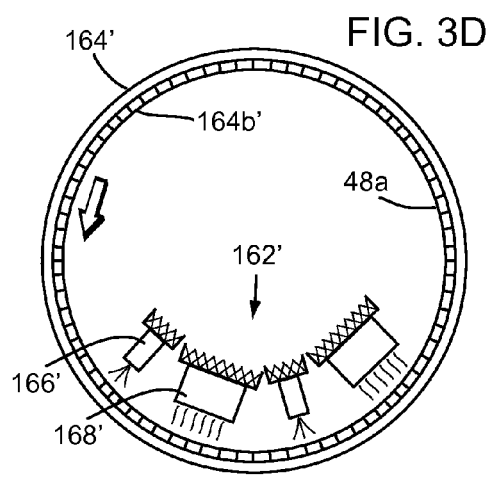

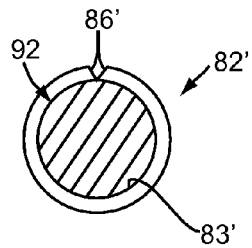
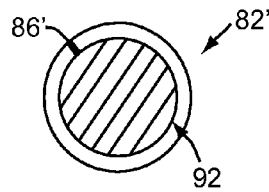
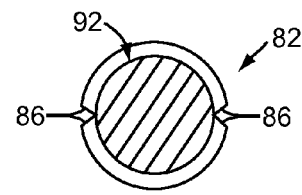
FIG. 8A  FIG. 9A  FIG. 10A
+  +  +
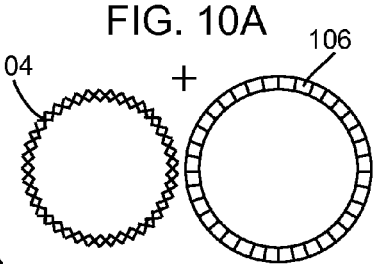
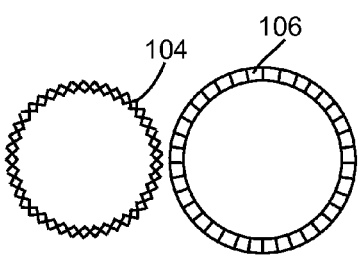
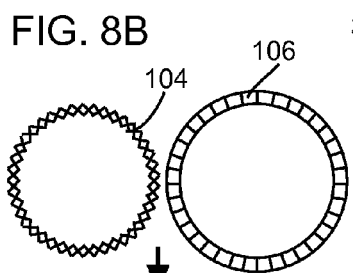
FIG. 8B
FIG. 9B
FIG. 10B
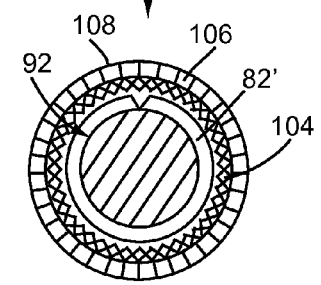
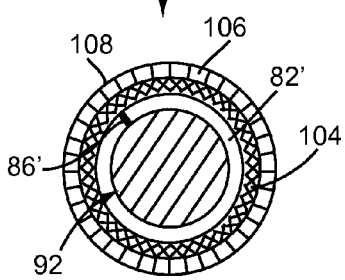
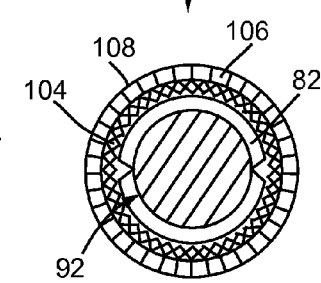
FIG. 8C  FIG. 9C  FIG. 10C
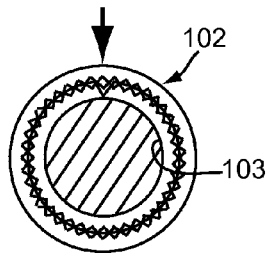
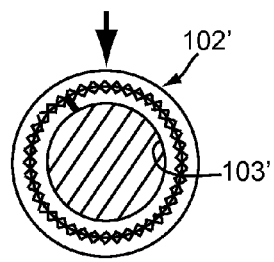
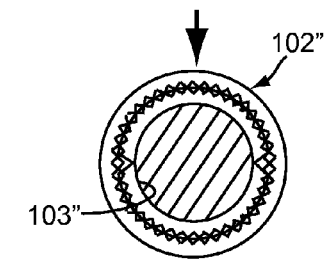
FIG. 8D  FIG. 9D  FIG. 10D

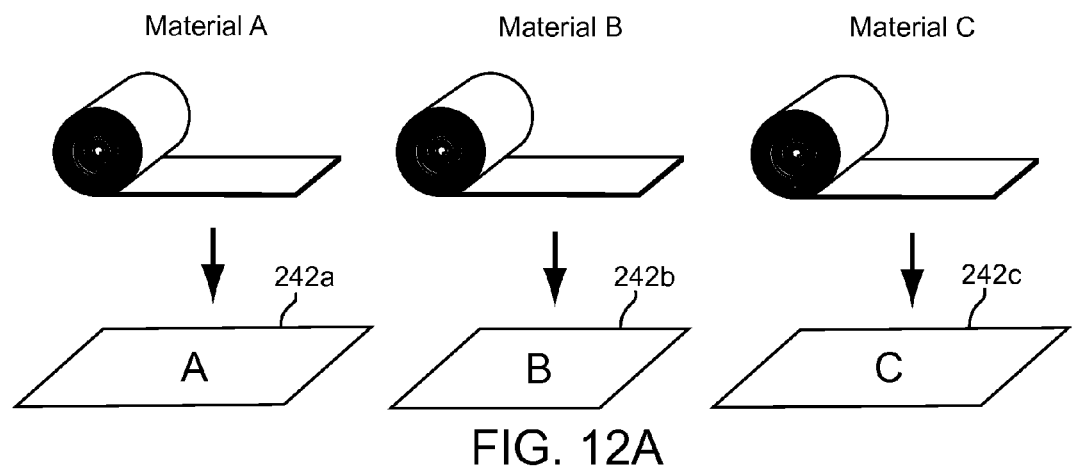
FIG. 12A
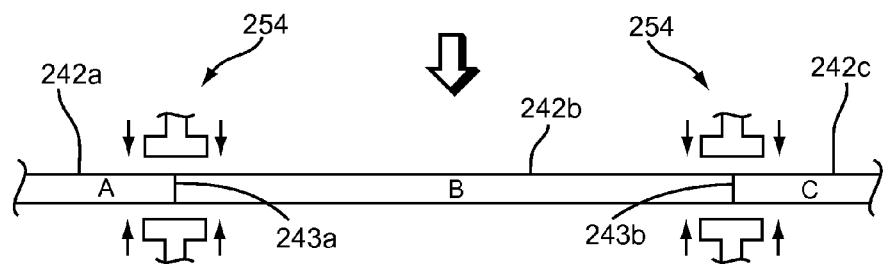
FIG. 12B
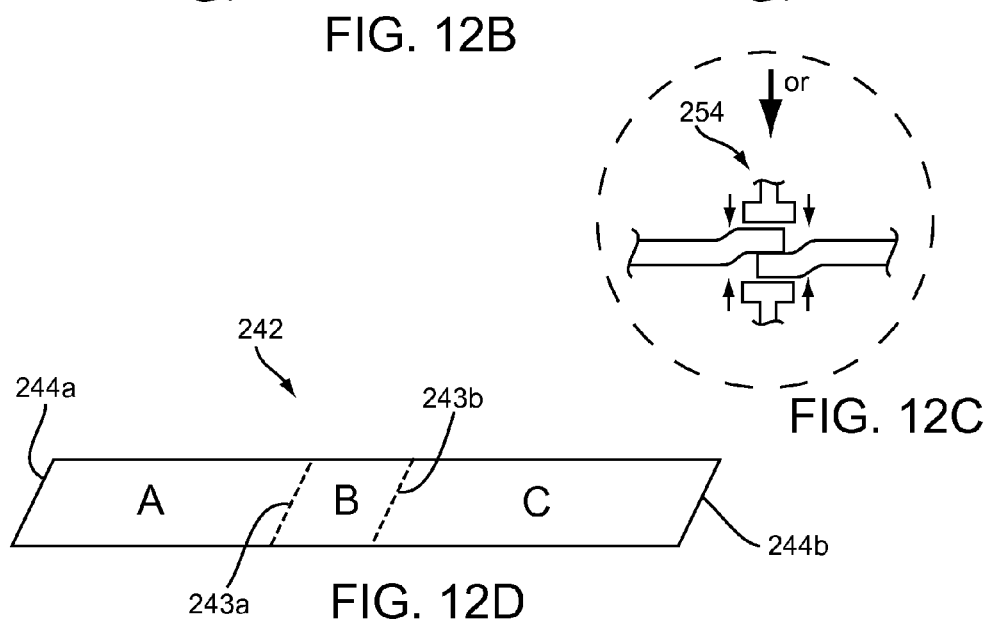
FIG. 12C
FIG. 12D

APPARATUS AND METHODS FOR MAKING COATED LINERS AND TUBULAR DEVICES INCLUDING SUCH LINERS

This application claims benefit of provisional application Ser. Nos. 61/153,295, filed Feb. 18, 2009, 61/223,352, filed Jul. 6, 2009, 61/227,745, filed Jul. 22, 2009, and 61/234,311, filed Aug. 16, 2009, the entire disclosures of which are expressly incorporated by reference herein.

FIELD OF THE INVENTION

The present invention relates generally to apparatus and methods for making catheters, sheaths, or other tubular devices, and, more particularly, to apparatus and methods for making coated liners for catheters, sheaths, or other tubular devices, and catheters, sheaths, or other tubular devices including coated liners.

BACKGROUND

Medical devices, such as catheters, sheaths, or other tubular devices, frequently have one or more inner lumens that partially or fully extend through the device. These lumens are routinely exposed to bodily fluids or tissues and/or interact with other instruments and/or physician specified fluids unique to a given device or procedure. Given the disparate uses of these lumens and subsequent wide variety in desired performance attributes, various materials and processes have been developed and explored to impart desired performance attributes. In spite of a wide variety of materials, including specialty coatings, the processes currently known for constructing catheters including desired performance attributes are generally limited and are frequently prohibitively complicated and/or expensive. For example, applying an anti-thrombogenic coating to the inner surface of a cardiovascular catheter device or subassembly may require 1) masking undesired parts of the catheter from exposure to the coating and/or 2) special curing processes like exposure to heat or Ultraviolet ("UV") light. However, heat may be damaging to other catheter components and/or it may be difficult to expose inner surfaces of small lumens to UV light even over modest lengths. Alternatively, constructions may include lubricious liners and/or hydrophilic coatings. These tedious processes, however, routinely exact compromises that reduce the effectiveness of the materials used or applied. Furthermore, these processes do not lend themselves to batch or mass production and therefore lack the associated benefits in cost and quality.

SUMMARY

The present invention is directed to apparatus and methods for making catheters, sheaths, or other tubular devices. More particularly, the present invention is directed to apparatus and methods for making coated liners for catheters, sheaths, or other tubular devices, and tubular devices including such coated liners.

In accordance with one embodiment, a tubular device is provided that includes a proximal end, a distal end sized for introduction into a body lumen, and a lumen extending between the proximal and distal ends. Generally, the tubular device includes an inner liner including a coating on an inner surface thereof, the coating imparting one or more predetermined properties to a wall of the lumen, a reinforcing layer surrounding at least a portion of the liner; and an outer layer surrounding the reinforcing layer and inner liner.

In one embodiment, the liner may include multiple sections having different properties than one another, adjacent sections being attached together by seams, and the outer layer may also include multiple sections having different properties than one another. If desired, the adjacent sections of the outer layer may be attached together by seams that are spaced apart axially from seams of the inner liner, e.g., to stagger the seams and/or provide smoother transitions on the distal end of the tubular member.

Optionally, the tubular device may include a distal tip attached to the distal end of the tubular device, the distal tip including an outer tubular layer surrounding a coated liner without a reinforcing layer. The materials of the distal tip may have different properties than the multiple sections of the inner liner and outer layer, e.g., having Durometers that are substantially softer than the adjacent sections of the distal end of the tubular device. For example, in one embodiment, the coated liner of the distal tip may comprise material that is softer than a distal-most section of the inner liner of the distal end and/or the outer tubular layer of the distal tip may comprise material that is softer than a distal-most section of the outer layer of the distal end.

In addition or alternatively, the multiple sections of the inner liner may include a relatively soft distal-most section and a relatively less soft shaft section attached to the distal-most section by a first seam. The first seam may be substantially orthogonal or non-orthogonal to a longitudinal axis of the tubular device. Alternatively, the first seam may include edges of the distal-most section and the shaft section that are interlocked with one another.

Similarly, the multiple sections of the outer layer may include a plurality of transition sections adjacent one another on the distal end and a shaft section that extends proximally from the transition sections. For example, the transition sections may include a first distal-most transition section, and a second transition section attached to the first transition section, the first transition section having a lower Durometer than the second transition section. Optionally, the transition sections may also include a third transition section attached between the second transition section and the shaft section, the second transition section having a lower Durometer than the third transition section.

In an exemplary embodiment, the multiple sections of the inner liner may comprise different color materials, e.g., to facilitate identifying transitions between the multiple sections.

In accordance with another embodiment, a tubular device is provided that includes a proximal end, a distal end sized for introduction into a body lumen, and a lumen extending between the proximal and distal ends. The tubular device may include an inner liner including a coating on an inner surface thereof, the coating imparting one or more predetermined properties to a wall of the lumen, a reinforcing layer surrounding at least a portion of the liner, and an outer layer surrounding the reinforcing layer and inner liner. The inner liner may include multiple sections attached together, wherein the multiple sections comprises different color materials to facilitate identifying transitions between the multiple sections, different Durometers, and/or different thicknesses.

In accordance with yet another embodiment, a tubular device is provided that includes a proximal end, a distal end sized for introduction into a body lumen, a lumen extending between the proximal and distal ends, and a distal tip attached to the distal end. The tubular device includes an inner liner comprising a coating on an inner surface thereof, the coating imparting one or more predetermined properties to a wall of the lumen. The liner also includes a transition section extending proximally from the distal tip, and a shaft section attached to the transition section, the transition section having different properties than the shaft section. In addition, the tubular device includes a reinforcing layer surrounding the liner; and an outer layer surrounding the reinforcing layer and inner liner. The outer layer may include one or more transition sections extending proximally from the distal tip and a shaft section attached to a proximal-most of the one or more transition sections. The distal tip may include an outer tubular layer surrounding a coated liner without a reinforcing layer, the material of the distal tip being softer than the transition sections of the inner liner and outer layer.

Optionally, the transition and shaft sections of the inner liner may be attached together at a seam, and adjacent sections of the outer layer may be attached together by seams that are spaced apart axially from seam of the inner liner. In addition or alternatively, the transition section of the inner liner may be softer than the shaft section of the inner liner, and/or the one or more transition sections of the outer layer may be softer than the shaft section.

In accordance with still another embodiment, a tubular device is provided that includes a proximal end, a distal end sized for introduction into a body lumen, and a lumen extending between the proximal and distal ends. The tubular device includes an inner liner comprising a coating on an inner surface thereof, the coating imparting one or more predetermined properties to a wall of the lumen. The inner liner may be formed from an enclosed band wrapped around a mandrel such that the inner liner defines a pair of longitudinal seams extending between the proximal and distal ends of the tubular device. In addition, the tubular device includes a reinforcing layer surrounding the liner; and an outer layer surrounding the reinforcing layer and inner liner.

Optionally, the enclosed band may include multiple sections having different properties such that the properties of the inner liner vary between the proximal and distal ends of the tubular device. In addition or alternatively, the outer layer may also include multiple sections having different properties than one another, adjacent sections being attached together by seams that are spaced apart axially from one or more seams separating the multiple sections of the inner liner.

In one embodiment, the longitudinal seams of the inner liner may extend substantially axially between the proximal and distal ends of the tubular device. Alternatively, the longitudinal seams of the inner liner extend helically between the proximal and distal ends of the tubular device. The longitudinal seams of the inner liner may include longitudinal edges that are spaced apart from one another to define gaps when the endless band is wrapped around the mandrel, the outer layer being reflowed to substantially fill the gaps between the longitudinal edges.

In accordance yet another embodiment, a method is provided for making a tubular device sized for introduction into a body lumen. An endless band of material including a coated surface may be folded such that the endless band defines first and second ends and the coated surface is disposed inwardly. The first and second ends of the endless band may be stretched or otherwise provided over opposite ends of an elongate mandrel such that the coated surface is disposed inwardly towards the mandrel and the endless band wraps partially around the mandrel such that longitudinal edges of the endless band extend between the opposite ends of the mandrel. A tubular structure may be attached around the endless band while wrapped around the mandrel, e.g., including a reinforcing layer and an outer tubular layer.

After attaching the tubular structure around the wrapped band, the enclosed ends of the endless band may be removed and/or the mandrel may be removed from the band to provide a tubular device defining a coated lumen.

In an exemplary embodiment, the endless band may be created by attaching first and second ends of a sheet together, mounting the resulting assembly to a coating apparatus, and applying a coating to at least one surface of the sheet.

In accordance with still another embodiment, a method is provided for making a tubular device sized for introduction into a body lumen that includes mounting an endless band to an apparatus that moves the band along an enclosed path including one or more coating elements; applying a coating to at least one of the inner surface and the outer surface using the one or more coating elements; and separating the endless band into a plurality of narrower endless bands after applying the coating.

One of the narrower bands may be folded such that the narrower endless band defines first and second ends and the coating is disposed inwardly. The first and second ends of the narrower band may be stretched or otherwise positioned over opposite ends of an elongate mandrel such that the coating is disposed inwardly towards the mandrel and the narrower endless band wraps partially around the mandrel such that longitudinal edges of the narrower endless band extend between the opposite ends of the mandrel. A tubular structure may then be attached around the narrower endless band while wrapped around the mandrel.

In accordance with another embodiment, a method is provided for making a tubular device sized for introduction into a body lumen that includes providing a sheet of material having first and second ends and longitudinal edges extending between the first and second ends, and attaching the first and second ends of the sheet together to create an endless band including an inner surface and an outer surface. The endless band may be mounted to an apparatus that moves the band along an enclosed path including one or more coating elements, and a coating may be applied to at least one of the inner surface and the outer surface using the one or more coating elements.

In one exemplary embodiment, the coating apparatus may include a drum including at least one of an interior surface and an exterior surface defining the enclosed path, and the endless band may be mounted to one of the interior and exterior surfaces of the drum. The coating may then be applied by rotating the drum to move the endless band past the one or more coating elements.

In another exemplary embodiment, the coating apparatus may include a roller assembly including a plurality of rollers defining the enclosed path, and the endless band may be mounted to the apparatus by extending the endless band between the plurality of rollers. The coating may then be applied by rotating one or more of the plurality of rollers to move the endless band along the enclosed path and past the one or more coating elements.

After coating, the endless band may then be separated into one or more liner components. For example, in one embodiment, the endless band may be cut or otherwise separated into one or more strips, and one of the strips may be wrapped around a mandrel such that the coating is disposed inwardly towards the mandrel. A tubular structure may then be attached around the wrapped strip and mandrel.

For example, ends of the strip may be secured to ends of the mandrel, and the strip may be wrapped around the mandrel in a longitudinal configuration, wherein longitudinal edges of the strip extend between the ends of the mandrel, e.g., in a longitudinal configuration. Alternatively, the strip may be wrapped helically around the mandrel between first and second ends of the mandrel.

In accordance with still another embodiment, a method is provided for making a tubular device sized for introduction into a body lumen that includes providing a sheet of material having first and second ends and longitudinal edges extending between the first and second ends; attaching the first and second ends of the sheet together to create an endless band including an inner surface and an outer surface; mounting the endless band to an apparatus that moves the band along an enclosed path including one or more coating elements; and applying a coating to at least one of the inner surface and the outer surface using the one or more coating elements. The endless band may be separated into a plurality of narrower bands after applying the coating, and each of the narrower bands may be wrapped around a mandrel such that the coating is disposed inwardly towards the mandrel and longitudinal edges of the band extend between ends of the mandrel. A tubular structure may then be attached around each of the wrapped bands.

In accordance with yet another embodiment, a method is provided for making a tubular device sized for introduction into a body lumen that includes providing a sheet of material having first and second ends and longitudinal edges extending between the first and second ends; attaching the first and second ends of the sheet together to create an endless band including an inner surface and an outer surface; mounting the endless band to an apparatus that moves the band along an enclosed path including one or more coating elements; and applying a coating to at least one of the inner surface and the outer surface using the one or more coating elements. The endless band may then be separated into one or more liner components after applying the coating, and each of the liner components may be wrapped around a mandrel such that the coating is disposed inwardly towards the mandrel. A tubular structure may then be attached around each of the wrapped liner components.

In accordance with still another embodiment, a method is provided for making one or more liner components for tubular devices sized for introduction into a body lumen. Initially, a plurality of endless bands may be provided, and a coating may be applied to at least a first surface of each of the endless bands. Optionally, at least one of the endless bands may be formed from a different material than one or more other endless bands and/or the coating applied to at least one of the endless bands may be different from a coating applied to one or more other endless bands. Each of the endless bands may be cut or otherwise separated into one or more sheets after applying a coating to each of the endless bands. At least one sheet from each of the endless bands may be attached together to create a composite sheet, and the composite sheet may be used to create a composite liner for a tubular device. For example, the composite sheet may be wrapped at least partially around a mandrel (alone or along with other composite sheets) to create a liner component, and a tubular structure may then be attached around the wrapped composite sheet.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIGS. 2A and 2B are perspective views of a sheet that may be formed into an endless band that may be used to make one or more liners.

FIGS. 2C and 2D are details showing a method for attaching ends of the sheet of FIGS. 2A and 2B to form an endless band.

FIG. 2E is a detail showing an alternate method for attaching ends of the sheet of FIGS. 2A and 2B to form an endless band.

FIGS. 2I and 2J are perspective and side views, respectively, of an exemplary embodiment of an endless band that may be used to make one or more liners.

FIG. 3A is a schematic of a first exemplary embodiment of an apparatus showing a process for coating an inner surface of an enclosed band, such as the band of FIGS. 2I and 2J.

FIG. 3B is a schematic of a second exemplary embodiment of an apparatus showing a process for coating an outer surface of an endless band.

FIG. 3C is a schematic of a third exemplary embodiment of an apparatus showing a process for coating an outer surface of an enclosed band.

FIG. 3D is a schematic of a fourth exemplary embodiment of an apparatus showing a process for coating an inner surface of an endless band.

FIG. 8A-8D are cross-sectional views of a coated sheet on a mandrel, such as that shown in FIG. 5B, having a reinforcing layer and an outer jacket provided around them to make a tubular member having a coated lumen.

FIG. 9A-9D are cross-sectional views of a coated sheet on mandrel, such as that shown in FIG. 6C, having a reinforcing layer and an outer jacket provided around them to make a tubular member having a coated lumen.

FIG. 10A-10D are cross-sectional views of a coated sheet on mandrel, such as that shown in FIG. 7F, having a reinforcing layer and an outer jacket provided around them to make a tubular member having a coated lumen.

FIG. 12A is a perspective view of rolls of different liner material being separated into individual sheets to be attached together to form a composite sheet.

FIG. 12B is a side view of the sheets of FIG. 12A, showing a method for attaching ends of the sheets to form a composite sheet.

FIG. 12C is a detail of an alternate method for attaching ends of the sheets of FIG. 12A to form a composite sheet.

FIG. 12D is a perspective view of the composite sheet resulting from the method of FIGS. 12A-12B.

DETAILED DESCRIPTION OF THE EXEMPLARY EMBODIMENTS

Figure 1A:
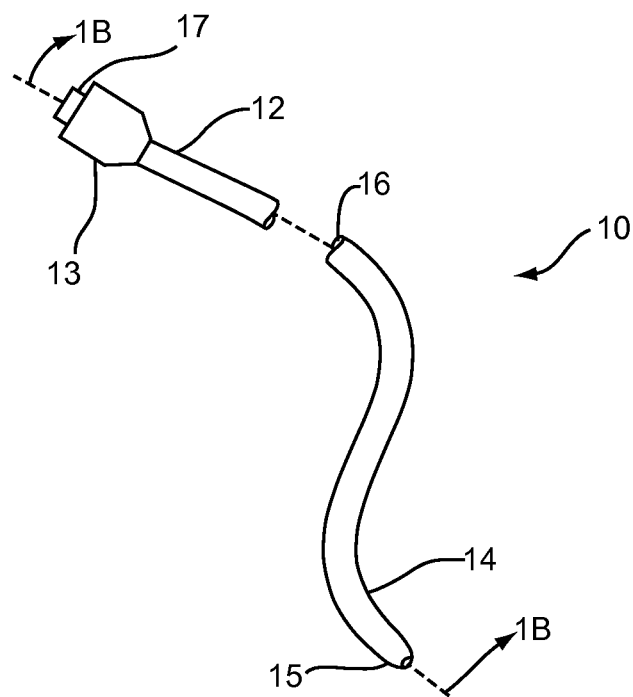
FIG. 1A is a perspective view of an exemplary embodiment of a tubular device, including a lumen extending between proximal and distal ends thereof.
Figure 1B:
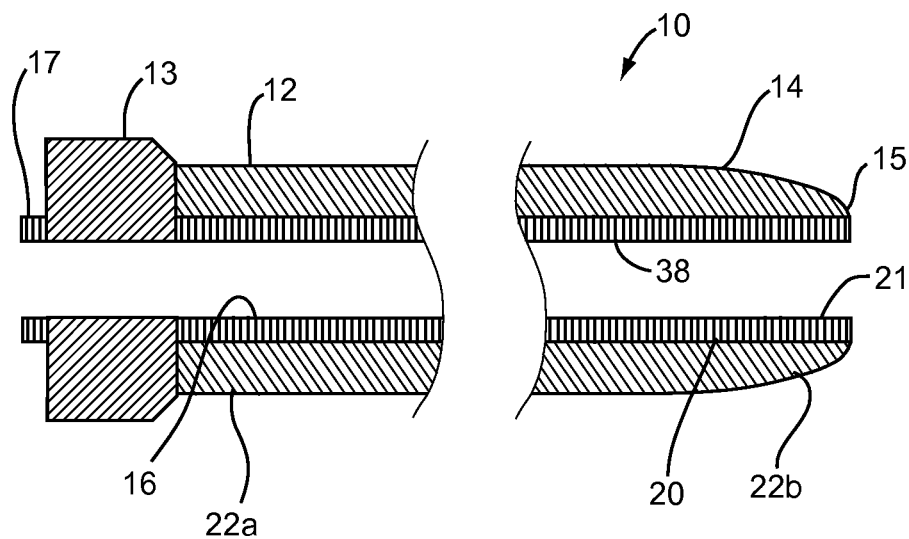
FIG. 1B is a cross-sectional view of the tubular device of FIG. 1A, taken along line 1B-1B, showing a coated liner surrounding the lumen and an outer layer surrounding the coated liner.

Turning to the drawings, FIGS. 1A and 1B show an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 is an elongate tubular member including a proximal end 12, a distal end 14 sized for insertion into a body lumen, and a lumen 16 extending between the proximal and distal ends 12, 14. Optionally, the apparatus 10 may include one or more additional lumens (not shown), which may be disposed concentrically around or side-by-side with the lumen 16. The lumen 16 may be sized for receiving a guide wire, procedure catheter, cardiac lead, needle, or other instrument (not shown), and/or for delivering fluids or other flowable agents or materials therethrough.

Optionally, the distal end 14 may include a tapered, rounded, or otherwise shaped distal tip 15, e.g., to provide a substantially atraumatic tip and/or facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, helical anchors, needles, and the like (not shown), depending upon the particular intended application for the apparatus 10.

Optionally, the proximal end 12 may include a handle 13 and/or one or more ports, e.g., port 17 communicating with the lumen 16. In addition or alternatively, the handle 13 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 13 may include one or more actuators, such as sliders, buttons, switches, and the like, e.g., for activating and/or manipulating components (also not shown) on the distal end 14 or otherwise operating the apparatus 10.

With particular reference to FIG. 1B, the apparatus 10 generally includes an inner liner 20 surrounding the lumen 16 and an outer layer 22 surrounding the inner liner 20. The inner liner 20 may include a relatively thin film, sheet, or other material including an inner surface 21. The inner surface 21 may include a coating 38 having one or more desired properties, e.g., a predetermined lubricity, hydrophilic characteristic, and the like, as described further below.

For example, the liner 20 may be formed from a single layer or multiple layers of material, e.g., having a thickness between about 0.0001-0.050 inch (0.0025-1.25 mm), 0.0001-0.01 inch (0.0025-0.25 mm), 0.0001-0.003 inch (0.0025-

0.076 mm), or 0.0001-0.0015 inch (0.0025-0.038 mm). In exemplary embodiments, the liner 20 may be formed from plastics, e.g., thermoplastics, such as polyether block amide ("PEBAX"), urethane, nylon, and the like, fluoropolymers, such as PTFE, FEP, TFE, and the like, thermoset, and thermoform plastics, such as polyimide or polyester, and the like. For example, the liner 20 may be Ether-based or Ester-based polyurethane. However, other suitable polymers may also be used, such as nylon (including nylon 6/6, nylon 11, nylon 12, PEBA) and engineered resins (including Zytel, Rilsan, Grilamid, Vestamid, Pebax), polyethylene, polyvinylchloride, fluoropolymers (including PTFE, FEP, PFA, PVDF, THV, ETFE, ECFE), polyethylene terepthalate polyester, polyolefin, polyetheretherketone, polypropylene, polyolefin, silicone, natural and synthetic rubbers, polystyrene, polycarbonate, polymethylmethacrylate, and the like. Alternatively, the liner 20 may be formed from thin metal sheets, such as stainless steel or Nitinol, or composite materials. Alternatively, the liner 20 may be formed from woven, mesh, or nonwoven materials or fabrics, such as nylon, polyester, Tyvek® (flash-spun high-density polyethylene fiber material), and the like.

The liner 20 may have a substantially homogenous construction, although, alternatively, the construction may vary along the length to provide desired properties, e.g., as described further below with reference to FIGS. 11A and 11B. For example, the durometer of material may vary along the length of the thin film sheet 30. Furthermore, the liner 20 may have one or more transition regions along its length, transitioning from one desired construction to another, including from one desired material to another.

One or more coatings 38 may be applied to the inner surface 21 of the liner 20 during fabrication. In an exemplary embodiment, the coating includes a hydrophilic material, such as Polyvinylpyrrolidone, and may be sprayed or otherwise applied onto the surface 21 during fabrication to apply a substantially uniform thickness coating. However, other suitable hydrophilic materials may also be used, including poly (ethylene oxide), poly(propylene oxide), poly(ethylene glycol), poly(n-vinyl lactam) polyacrylamide, methylcellulose, hydroxypropyl cellulose, hydroxypropylmethyl cellulose, polyacrylic acids, hydroxyethyl methacrylate, polyvinyl alcohols, polyvinyl ethers, hyaluronan, polyurethanes, silicone hydrogel, soy-based hydrogels, and fluorocarbon-sulfone compounds.

The hydrophilic material may provide a predetermined lubricity on the inner surface 21. Alternatively, other materials may be applied to provide one or more desired properties on the inner surface 21 e.g., lubricious, biocompatible, hemocompatible, antithrombotic, procoagulant, antimicrobial, antibiotic, anti-encrustive, pH modulating, growth promoting, growth inhibiting, antiproliferative, endothelialization promoting, cell adhesion promoting, MR signal emitting, radiodense, echogenic, catalytic, immune modulating, antihemolytic, drug-eluting, drug delivery, and the like.

Following application of the coating 38 on the inner surface 21, e.g., using any of the apparatus and methods described elsewhere herein, the coating may be cured, cross-linked, or otherwise processed to increase the strength of adhesion of the coating 38 to the surface 21, e.g., using heat, ultraviolet ("UV") light, chemical processing, and the like, as described further below.

The outer layer 22 may be attached to the inner liner 20, e.g., by laminating, adhering, adhesive bonding, ultrasonic welding, reflowing or other heating, and the like, as described elsewhere herein.

Optionally, the outer layer 22 may include one or more sublayers (not shown). For example, the outer layer 22 may include a braided or helical reinforcing layer (not shown) surrounding the inner liner 20 and one or more tubular layers (also not shown) surrounding the reinforcing layer and/or between the reinforcing layer and the inner liner 20. In exemplary embodiments, the reinforcing layer may include one or more round or flat wires, filaments, strands, and the like, e.g., formed from metal, such as stainless steel, plastic, woven fibers, such as glass, Kevlar, and the like, or composite materials. Materials that may be used in the outer layer 22 include doped or undoped PEBAX, urethane, nylon (including nylon 6/6, nylon 11, nylon 12, PEBA) and engineered resins (including Zytel, Rilsan, Grilamid, Vestamid), polyethylene, polyvinylchloride, fluoropolymers (including PTFE, FEP, PFA, PVDF, THV, ETFE, ECFE), polyethylene terephthalate polyester, polyetheretherketone, polypropylene, silicone, natural and synthetic rubbers, polystyrene, polycarbonate, polymethylmethacrylate, and the like. Materials may be primarily selected for optimal mechanical, bonding, and/or other properties and subsequently imparted with desired surface properties, for example lubricity, by coating.

Exemplary outer layers that may be included in the apparatus 10 and methods for making them are disclosed in U.S. Pat. Nos. 4,478,898, 4,863,442, 5,217,440, 5,254,107, 5,676,659, 5,811,043, 5,836,926, 6,004,310, 6,669,886, 6,837,890, and 6,945,970. The entire disclosures of these references are expressly incorporated by reference herein.

The outer layer 22 may have a substantially homogenous construction between the proximal and distal ends 12, 14. Alternatively, the construction may vary along the length of the apparatus 10 to provide desired properties. For example, the outer layer 22a at or adjacent the proximal end 12 may be substantially rigid or semi-rigid, e.g., providing sufficient column strength to allow the apparatus 10 to be pushed from the proximal end 12. In addition, the reinforcing layer or other material in the outer layer 22 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking Optionally, the outer layer 22b at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer 22a, may have one or more transition regions along its length, transitioning from one desired construction to another.

In exemplary embodiments, the apparatus 10 may have an outer diameter between about half and twenty millimeters (0.5-20 mm), and a length between about five and one hundred fifty centimeters (5-150 cm). The inner liner 20 may have a wall thickness between about 0.0001-0.01 inch (0.0025-0.25 mm) and the outer layer 22 may have a wall thickness between about 0.0005-0.2 inch (0.0127-5.08 mm).

Figure 1C:
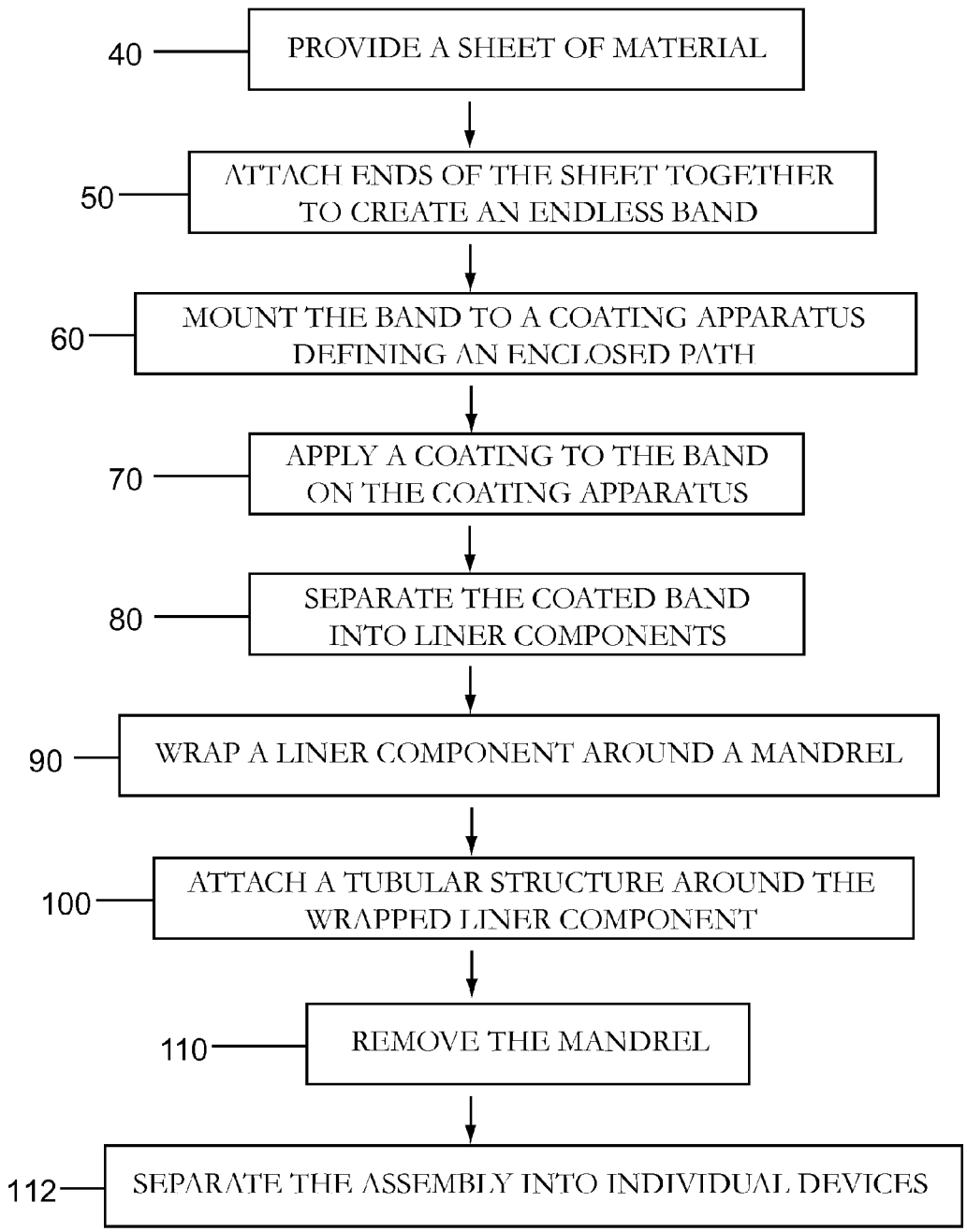
FIG. 1C is a flow chart showing an exemplary method for making tubular devices, such as the tubular device of FIGS. 1A and 1B.

Turning to FIG. 1C, an exemplary method is shown for making one or more tubular devices, such as the apparatus 10 of FIGS. 1A and 1B. Initially, at step 40, a sheet of material may be provided, e.g., that may be used to make the inner liner 20 of the apparatus 10. An exemplary embodiment of a sheet of material 42 is shown in FIGS. 2A and 2B. As shown, the sheet 42 includes first and second ends 44a, 44b, longitudinal edges 46a, 46b extending between the first and second ends 44a, 44b, and first and second surfaces 48a, 48b. In this embodiment, the sheet 42 may include a substantially uniform construction, e.g., being formed from a single material having a substantially uniform thickness and mechanical properties. Alternatively, the material, mechanical properties, thickness, durometer, color, and/or other properties of the sheet 42 may be varied, e.g., along its length between the first and second ends 44a, 44b, as described further below. Properties of the sheet may be varied to impart desirable properties to a tubular device or other apparatus into which the sheet is incorporated as a liner, or may be varied to aid in fabrication. For example, varying color along with other properties may enable easy identification or alignment of transitions and/or identification of coated surfaces during processing or assembly of the sheet.

Returning to FIG. 1C, at step 50, ends of the sheet intended to create one or more liners may be attached together to create an endless band. For example, as shown in FIGS. 2B-2J, the first and second ends 44a, 44b of the exemplary sheet 42 are shown being attached together to create an endless band 52. In this example, the first surface 46a of the sheet 42 defines an inner surface of the band 52 and the second surface 46b defines an outer surface of the band 52.

Figure 2F:
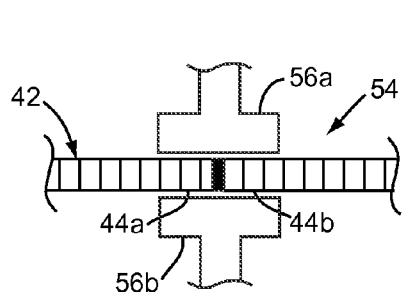
FIGS. 2F-2H are details showing additional alternate methods for attaching ends of the sheet of FIGS. 2A and 2B to form an endless band.
Figure 2G:
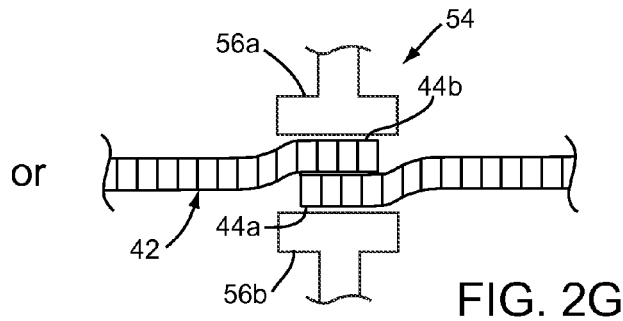
Figure 2H:
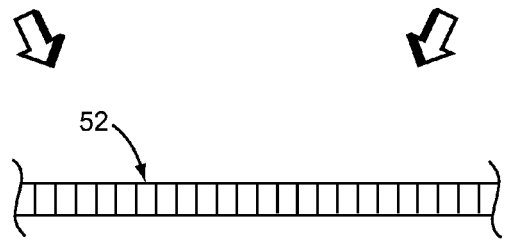
Figure 2I:
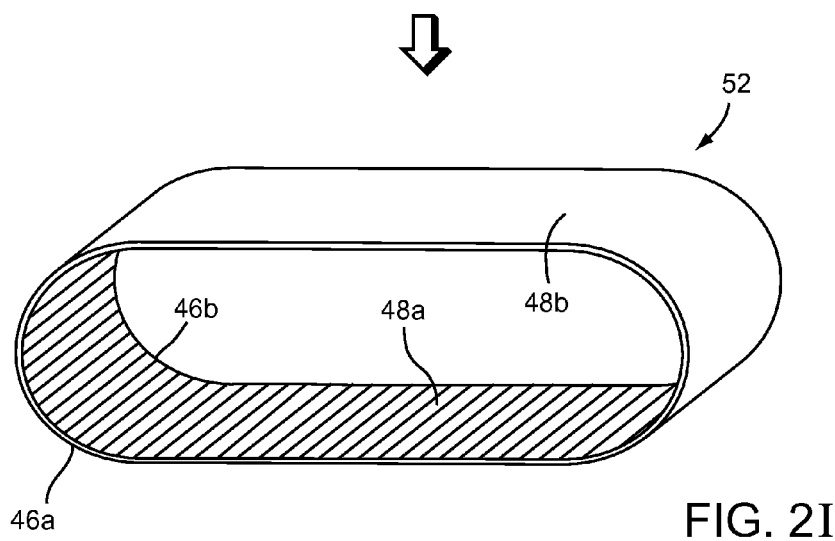

With particular reference to FIGS. 2C and 2D, the first and second ends 44a, 44b may be butted together and attached, for example, by welding (e.g., sonic welding), fusing (e.g., heating, melting, or otherwise reflowing the material), bonding with adhesive, and the like. Alternatively, the ends 44a, 44b may be attached together using one or more fasteners, e.g., staples, clips, threads, tape, and the like (not shown), which may facilitate separating the ends 44a, 44b of the sheet 42 after processing the endless band 52, if desired. FIG. 2F shows an exemplary embodiment of a heating assembly 54 including first and second plates 56a, 56b that may be used to fuse the butted ends 44a, 44b. FIGS. 2E and 2G show an alternative process in which the ends 44a, 44b of the sheet 42 are lapped over one another by a desired distance and attached together, e.g., using the heating assembly 54. In either option, the resulting seam may have a substantially uniform thickness, similar to the rest of the sheet 42 creating the band 52, e.g., as shown in FIGS. 2H-2J. Thus, the resulting band 52 may have a substantially uniform thickness and/or other substantially homogeneous mechanical properties. Alternatively, the thickness of the seam may be greater or otherwise not the same as the rest of the sheet 42, e.g., if the seam is not intended to be used as part of a liner for a tubular device (not shown) or if the seam is reflowed to a similar thickness to the sheet 42 during subsequent processing, e.g., as described elsewhere herein.

Alternatively, an endless band may be created by methods other than attaching together ends of a sheet. For example, an extruded tube (not shown) may be cut in relatively short lengths and stretched, blown, or otherwise expanded to increase its diameter. Alternatively, an endless band may be created from multiple relatively narrower endless bands or one or more strips joined with a helical seam, e.g., as described below.

Returning to FIG. 1C, at step 60, the endless band may be mounted to a coating apparatus, e.g., which may define a substantially enclosed path. Once the endless band is mounted to the coating apparatus, at step 70, one or more coatings may be applied to at least one of the inner surface and the outer surface of the band using the coating apparatus. The coating(s) may be applied to the surface(s) substantially continuously, i.e., by directing the endless band around the enclosed path one or more times. A single pass or circuit is completed when any point on the endless band passes from a starting point along the entire length of the enclosed path and returns to the starting point.

For example, FIG. 3A shows an exemplary embodiment of a coating apparatus 62 that includes a roller assembly including a plurality of rollers or pulleys 64 and one or more coating elements 66, 68. The rollers 64 may be spaced apart from one another to define a substantially enclosed path along which the endless band 52 may be mounted and directed. At least one of the rollers 64 may include a motor or other drive mechanism (not shown) for pulling or otherwise directing the endless band 52 along the enclosed path. In addition, one or more of the rollers 64 may be spatially adjustable, for example, movable manually or automatically relative to the other rollers 64, to adjust tension of the endless band 52, e.g., to maintain a desired tension to facilitate directing the endless band 52 along the enclosed path. For example, as shown in FIG. 3A, a tensioning roller 64a may apply tension to the endless band 52 based on its weight or additional added weight (e.g., by gravity), using a spring assembly (not shown), and the like.

The rollers 64 may have a width corresponding to the width of the endless band 52, e.g., between about 0.005 to ninety six inches (0.005-96"), or between about two to twelve inches (2-12"). For example, the width of the rollers 64 may correspond to the circumference of individual liners, to the circumference of multiple liners or to the length of individual liners being formed from the endless band 52. Optionally, the rollers 64 may include sprockets or other features for positively engaging the endless band 52, although alternatively, the material of the rollers 64 may itself allow the endless band 52 to be directed around the rollers 64 with minimal slippage.

Generally, the coating element(s) include one or more applicators 66 for applying one or more coating materials to an inner surface 48a of the endless band 52, and one or more curing devices 68 for curing the coating material. As shown, the coating apparatus 62 includes a first applicator 66a and curing device 68a spaced apart along the enclosed path from a second applicator 66b and curing device 68b. The applicators 66 may apply the same coating material or different materials, e.g., to provide a multiple layer coating on the endless band 52. For example, in one embodiment, the first applicator 66a may apply an initial coating of hydrophilic material, which may facilitate adhesion and/or uniform coverage or a second coating of hydrophilic material applied by the second applicator 66b. In another example, the first applicator 66a may apply a first therapeutic agent (e.g., an antiproliferative agent) and the second applicator 66b may apply a second therapeutic agent (e.g., an anti-thrombotic agent) over the first therapeutic agent. In still another example, one or more primers may be applied before applying one or more desired coatings. Alternatively, only a single applicator 66 and curing device 68 may be provided (not shown), for example, to provide a single coating layer, e.g., by passing the endless band 52 only once past the applicator 66 and curing device 68, although multiple layers may also be applied in such a configuration by simply directing the endless band 52 around the enclosed path multiple times. In a further alternative, a plurality of applicators 66 may be located before a single curing device 68 (not shown).

In exemplary embodiments, the applicator(s) 66 may include one or more sprayers, rollers, brushes, sponges, dipping assemblies, mayer rods, silk screening devices, spin coating devices, plasma coating devices, vapor deposition devices, and the like, e.g., as appropriate to apply a desired coating material to the endless band 52. The curing device(s) 68 may include one or more heating elements, sources of ultraviolet light, blowers, humidifiers, dryers, and the like, as appropriate to cure the coating material applied before the respective curing device 68. Alternatively, one or more of the curing device(s) 68 may be eliminated, e.g., if the coating material cures automatically.

Turning to FIG. 3B, another embodiment of a coating apparatus 62' is shown, which is generally similar to the coating apparatus 62 shown in FIG. 3A, except that the applicators 66' and curing devices 68' are located to apply a coating to an outer surface 48b of the endless band 52. Otherwise, the coating apparatus 62' may include similar components and may function similarly to the coating apparatus 62.

Turning to FIG. 3C, still another embodiment of a coating apparatus 162 is shown. Generally, the coating apparatus 162 includes a drum or other rotor 164 including a circumference around which the endless band 52 may be mounted, and one or more coating elements 166, 168 along the enclosed path for applying one or more coating materials to an outer surface 48b of the endless band 52. For example, as shown, the coating elements include two applicators 166 for applying coating material(s) and two curing devices 168, spaced apart from one another adjacent the drum 164, e.g., in first and second sets similar to the coating apparatus 62, although alternatively, only a single applicator 166 and curing device 168 may be provided or multiple applicators and curing devices, as desired (not shown).

In this embodiment, the endless band 52 may be wrapped around an outer surface 164a of the drum 164, which may have a fixed diameter and/or circumference, or may be adjustable to adjust a tension of the endless band 52 wrapped around the drum 164. In addition or alternatively, the endless band 52 may be stretched slightly to mount the endless band 52 around the drum 164, e.g., to secure the endless band 52 around the drum 162 by friction. Optionally, the endless band 52 may be substantially fixed to outer surface 164a of the drum 164 using one or more other features, e.g., a low-tack adhesive, vacuum ports in the drum 164 to pull the endless band 52 against the outer surface 164a, one or more fasteners, e.g., clamps or clips applied along the edges of the endless band 52, studs or other fasteners that penetrate through the material of the endless band 52, magnetic fasteners placed over the endless band 52 that are attracted to the drum 164 material, and the like (not shown).

With the endless band 52 mounted to the drum 162, the drum 162 may be rotated, thereby directing the endless band 52 along an enclosed path corresponding to the circumference of the drum 162. The applicator(s) 166 and curing device (s) 168 may be spaced apart in desired sets or configurations, similar to those described above to apply and cure one or more coating materials to the outer surface 48b of the endless band 52.

Turning to FIG. 3D, yet another embodiment of a coating apparatus 162' is shown that includes a drum 164' and one or more applicators 166' and curing devices 168' similar to the embodiment of FIG. 3C. Unlike the previous embodiment, however, the endless band 52 may be mounted to an inner surface 164b' of the drum 164' rather than an outer surface. In this alternative, fasteners may be needed to removably secure the endless band 52 to the inner surface 164b.' Otherwise operation of the coating apparatus 162' may proceed similar to the previous embodiment.

The drums 164, 164' may have a diameter between about twelve and thirty six inches (12-36"), e.g., at least two inches (2") to provide sufficient space to accommodate applicators, curing devices, and/or other components in or around the drums 164, 164' or as large as ten feet (10') in diameter to facilitate large production quantities. The drums 164, 164' may be formed from substantially rigid materials, e.g., a continuous fixed cylinder defining the outer or inner surfaces 164a, 164b.' Alternatively, the drums 164, 164' may include a plurality of plates, each defining a portion of a cylinder, that are arranged adjacent one another to approximate the enclosed path, e.g., with one or more of the plates being movable radially inwardly or outwardly to adjust the circumference of the enclosed path to correspond to the periphery of the endless band being coated and/or otherwise adjust tension of the endless band 52.

Optionally, after any of the coating processes just described, the coated band 52 may be cured or otherwise treated. For example, the coated band may be placed in a chamber and heated, exposed to ultraviolet light, and the like to further cure the coating and/or treat the material of the endless band 52. Alternatively, the endless band 52 may remain on the drum 164, 164' after coating and subjected to subsequent processing. For example, the drum 164, 164' may be removed from a drive axle (not shown) of the coating assembly 162, 162' and moved to another axle or device (not shown), e.g., for additional curing or processing. If desired, the subsequent axle or device may be in an environmental chamber to subject the endless 52 band to desired environmental conditions, e.g., heat, pressure, and/or humidity, compared to those used during the initial coating process. In an exemplary embodiment, a coating may be applied and partially cured using the coating assembly 162, 162' and the drum 164, 164' and coated band may be transferred to an oven (not shown) for additional curing.

Figure 4A:
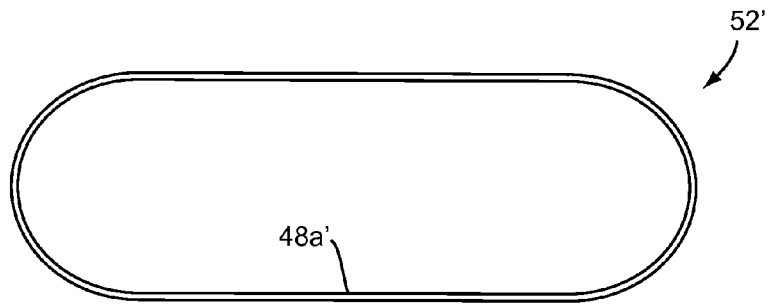
FIGS. 4A and 4B show an exemplary embodiment of an endless band being separated into one or more strips having a coated surface.
Figure 4B:
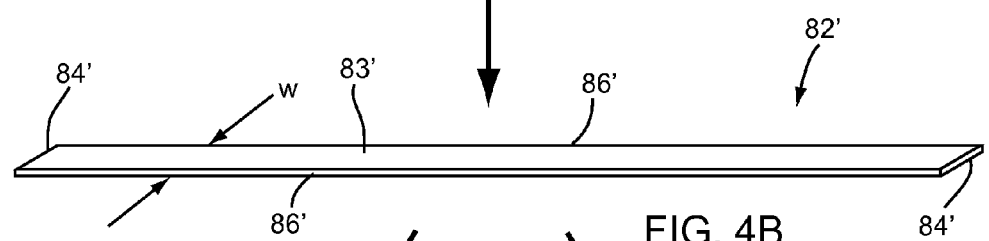

Returning to FIG. 1C, at step 80, the endless band 52 may be separated into one or more liner components. For example, in FIG. 4A, an endless band 52' is shown that has a width corresponding to a circumference of a desired liner. The band 52' may be cut, e.g., between its longitudinal edges to provide a relatively long, narrow strip 82,' as shown in FIG. 4B. Alternatively, the band 52' may have a width greater than individual liners, and may be cut into multiple narrow strips, as described further elsewhere herein.

Figure 7A:
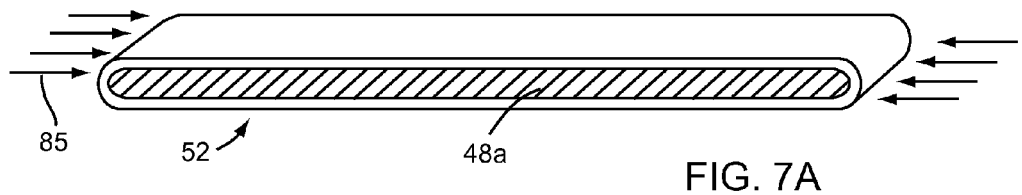
FIGS. 7A and 7B are perspective and side views, respectively, of an endless band having a coated surface being separated into a plurality of narrower endless bands.
Figure 7B:
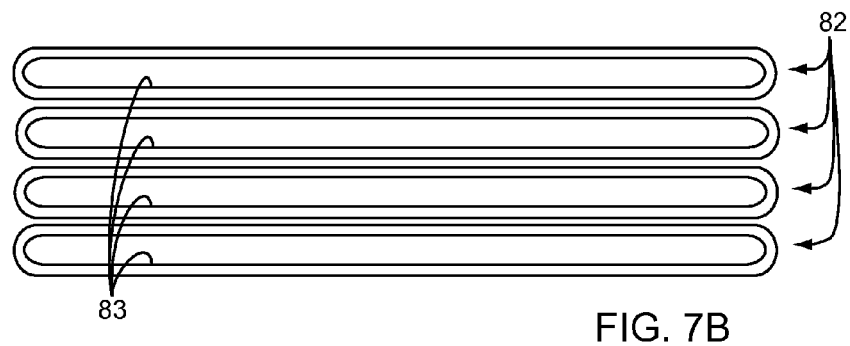

Alternatively, as shown in FIG. 7A, an endless band 52 having a width that is substantially greater than the circumference of a desired liner may be separated into a plurality of relatively narrower bands 82, as shown in FIG. 7B. For example, the endless band 52 may be cut using a plurality of cutting elements 85, shown schematically in FIG. 7A. The cutting elements may include a plurality of blades, wires, lasers, or other cutters capable of cutting through the material of the endless band 52. In one embodiment, the endless band 52 may be folded substantially flat, as shown in FIG. 7A, and directed past an array of cutting elements 85 that substantially simultaneously cut the endless band 52 into the narrower bands 82. Alternatively, narrower bands 82 may be cut from the endless band 52 sequentially using a single cutting element (not shown).

Figure 16A:
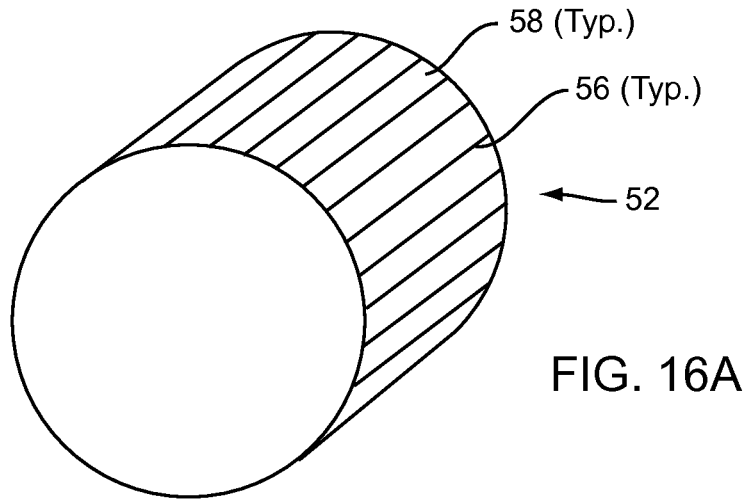
FIG. 16A is a perspective view of a coated endless band, showing axial cut lines for separating the endless band into a plurality of strips.
Figure 16B:
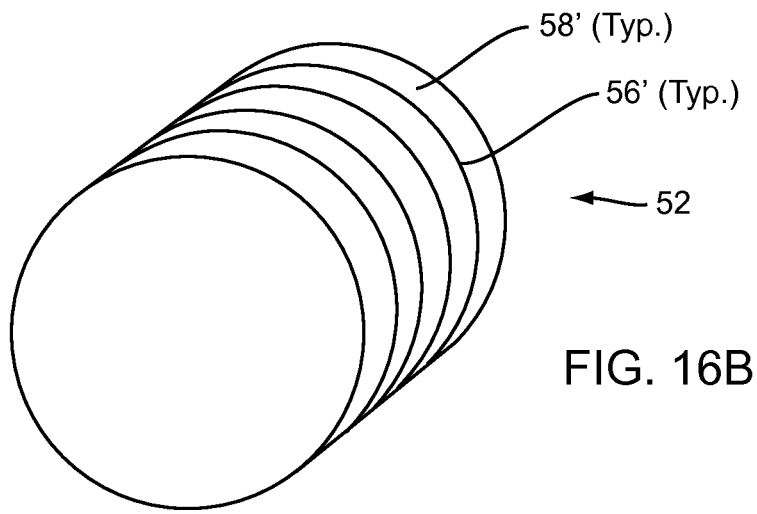
FIG. 16B is a perspective view of a coated endless band, showing circumferential cut lines for separating the endless band into a plurality of narrower endless bands.
Figure 16C:
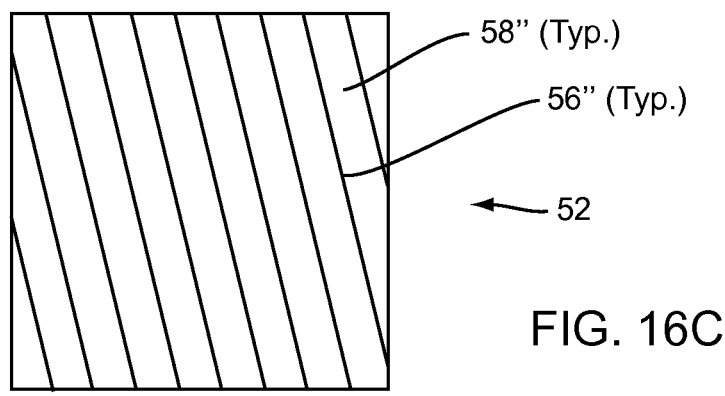
FIG. 16C is a perspective view of a coated endless band, showing a helical cut line for separating the endless band into a single continuous strip.

Turning to FIGS. 16A-16C, the endless band 52 may be separated into liner components in different configurations. For example, as shown in FIG. 16A, an endless band 52 may be cut or otherwise separated along axial cut lines 56 to create multiple strips 58. In this embodiment, the width of the endless band 52 corresponds to the lengths of the strips 58, e.g., which may correspond to the length of one or more liners being formed from the strips 58.

Alternatively, in FIG. 16B, the endless band 52 may be cut or otherwise separated along circumferential cut lines 56' to create multiple relatively narrow bands 58.' In a further alternative shown in FIG. 16C, the endless band 52 may be cut or otherwise separated along a helical cut line 56" to create a single continuous strip 58." Such a continuous strip 58" may be useful for making a plurality of tubular devices using a substantially continuous process, as described elsewhere herein. Alternatively, these processes may be reversed to create an endless band from two or more relatively narrower endless bands or one or more strips. For example, one or more circumferential seams (not shown) may be created between two or more relatively narrow bands 58' to create an endless band 52. Alternatively, a helical seam (not shown) may be created between one or more strips 58" to create an endless band 52. An endless band 52 created in this manner may be further coated, separated into liner components, or otherwise processed as described elsewhere herein.

In yet another alternative, one or more endless bands 52 may be cut or otherwise separated into one or more sheets, such as those depicted in FIG. 12A, and subsequently joined to form a single composite sheet 152 such as that shown in FIG. 12D having different properties along its length, as described further below. The sheet 152 may then be further separated into one or more liner components, also as described further below.

Returning to FIG. 1C, at step 90, one or more liner components created from the endless band may be formed into one or more liners and/or tubular devices. Generally, this involves wrapping each liner component around a mandrel, e.g., such that the coating is disposed inwardly towards the mandrel. Thereafter, at step 100, a tubular structure may be attached around the wrapped liner component and mandrel, e.g., to provide one or more tubular devices, such as the tubular device 10 shown in FIGS. 1A and 1B.

For example, turning to FIG. 4A-5B, an exemplary method for creating a coated liner is shown. As explained above, FIG. 4A shows an exemplary embodiment of an endless band 52' including a coated surface 48a' and FIG. 4B shows the endless band 52' cut to provide an elongated strip 82' including a coated surface 83.' The endless band 52' may have been formed and coated using any of the processes described above, or may have been created by separating a wider endless band (not shown) into a plurality of bands similar to band 52.' For example, a relatively wide endless band may be cut to provide a coated sheet, and then the sheet may be cut into individual strips, similar to strip 82.' For example, the coated sheet may be directed through an array of cutters, e.g., blades or wires, laser devices, and the like (not shown), that simultaneously creates a plurality of strips from the coated sheet.

Figure 5A:
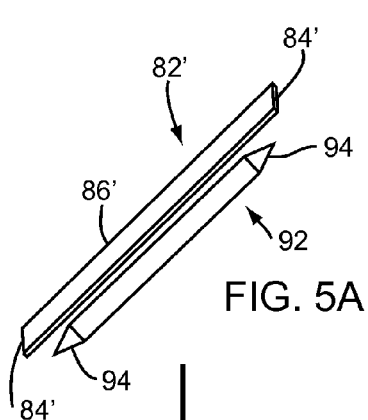
FIGS. 5A and 5B are perspective and cross-sectional views, respectively, of a strip from the band of FIGS. 4A and 4B being wrapped around a mandrel in a longitudinal configuration with the coated surface oriented inwardly towards the mandrel.
Figure 5B:
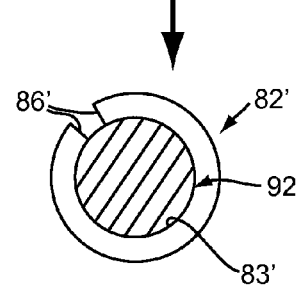

With additional reference to FIGS. 5A and 5B, the strip 82' may have a width "w" corresponding to a circumference of a liner to be formed using the strip 82'. More particularly, the width "w" of the strip may be substantially the same as the circumference of a mandrel 92. The strip 82' may have a length equal to or greater than a length of the mandrel 92 such that ends 84' of the strip 82' may be disposed adjacent respective ends 94 of the mandrel 92, e.g., such that longitudinal edges 86' of the strip 82' extend axially, e.g., substantially parallel to a longitudinal axis of the mandrel 92. As best seen in FIG. 5B, the strip 82 may then be wrapped around the mandrel 92 until the longitudinal edges 86' are disposed adjacent one another. For example, as shown in FIG. 5B, the inner most corners of the longitudinal edges 86' may contact one another or may be spaced slightly apart from one another (not shown), while the outer most corners of the longitudinal edges 86' are spaced apart from one another. Thus, the strip 82' may be wrapped around the mandrel 92 without the longitudinal edges 86 overlapping. Alternatively, the width "w" of the strip 82' may be slightly smaller than the circumference of the mandrel 92 such that a narrow gap (not shown) remains between the longitudinal edges 86' after wrapping the strip 82' around the mandrel 92. Alternatively, the longitudinal edges 86' may be modified such that any gap does not define a substantially straight line between the ends 84' of the strip 82.' For example longitudinal edges 86' may be cut in a sine-wave or zigzag pattern (not shown) such that one edge mirrors the other when the strip 82' is positioned around the mandrel 92.

Optionally, the ends 84' of the strip 82' may be secured relative to the mandrel 92. For example, in one embodiment, the ends 94 of the mandrel 92 may be pointed, and the ends 84' of the strip 82' may be hooked at least partially around the ends 94 of the mandrel 92, e.g., stretching the strip 82' to apply a slight tension along the length of the strip 82' between the ends 84.' Such tension may enhance maintaining the strip 82' wrapped around the mandrel 92 and/or aligning the longitudinal edges 86' along the mandrel 92.

Turning to FIGS. 8A-8D, the strip 82' wrapped around the mandrel 92 may be used to make a tubular device 102, which may be similar to tubular device 10 shown in FIGS. 1A and 1B. For example, as shown in FIGS. 8A-8C, a reinforcing layer 104 and an outer layer 106 may be placed around the strip 82,' e.g., surrounded by a section of heatshrink tubing 108. The entire assembly may be heated to reflow the outer layer 106, e.g., which may flow inwardly through the reinforcing layer and bond to the strip 82', filling any gap between the longitudinal edges 86' of the strip 82.' Exemplary methods for making tubular devices including reinforcing layers and outer layers are disclosed in U.S. Pat. Nos. 7,550,053 and 7,553,387, the entire disclosures of which are expressly incorporated by reference herein.

Returning to FIG. 1C, once the tubular device 102 of FIGS. 8C and 8D is made, at step 110, the mandrel 92 may be removed, along with the heatshrink tubing 108. The resulting tubular device 102 thus includes a lumen 103 surrounded by a coated liner defined by strip 82.' If the tubular device 102 has a length greater than a desired catheter or other finished device, the tubular device 102 may be separated into one or more devices at step 112. This may simply involve cutting the tubular device 102 into desired lengths, or any desired additional features desired for the finished device, such as those described above, may be added to the individual tubular devices 102, e.g., a relatively soft distal tip, a handle, a valve, a shape-set to the distal end, an outer diameter coating, one or more radiopaque markers, and the like (not shown).

Alternatively, the tubular device 102 may be made using a substantially continuous process. For example, if the endless band 52' in FIG. 4A is sufficiently long, the resulting strip 82' shown in FIG. 5A may be wound onto a reel and the like (not shown). The wound strip and reel may then be mounted on a spindle or other feature of an automated apparatus capable of feeding the strip along with other components of the tubular device 102 substantially continuously. Thus, the strip 82' may be used to make a sufficiently long tubular device 102 that may be separated into as few as one or as many as hundreds or thousands of tubular bodies, e.g., by substantially simultaneously feeding components of the tubular bodies from sources, such as reels, through the apparatus until the sources are depleted, whereupon new source(s) may be loaded onto the apparatus and the process continued. Thus, the apparatus and methods described herein may be used to make relatively long tubular bodies, e.g., that are substantially longer than finished catheters or other tubular devices. Exemplary apparatus and methods for such substantially continuous fabrication are disclosed in U.S. Publication No. 2009/0126862, published May 21, 2009, the entire disclosure of which is expressly incorporated by reference herein.

Figure 6A:
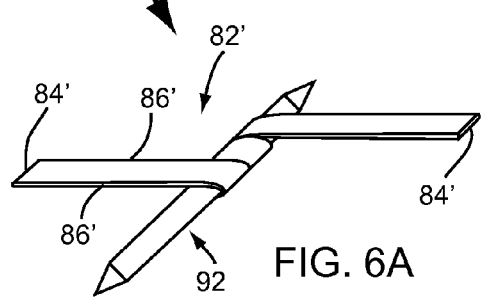
FIGS. 6A and 6B are perspective views and FIG. 6C is a cross-sectional view of a strip from the band of FIGS. 4A and 4B being wrapped around a mandrel in a helical configuration with the coated surface oriented inwardly towards the mandrel.
Figure 6B:
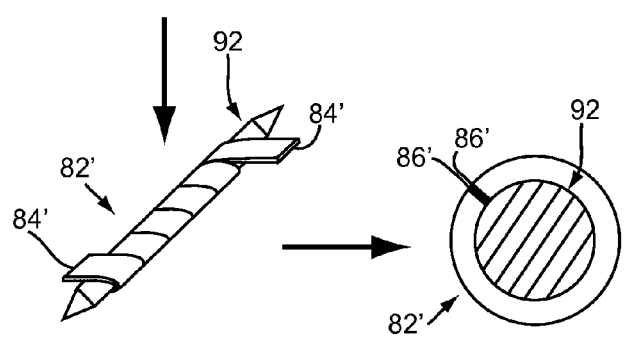
Figure 6C:
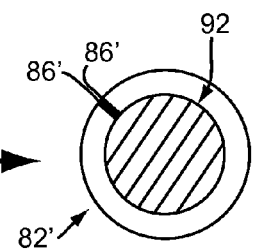

Returning to FIGS. 4A and 4B, with additional reference to FIGS. 6A-6C, another method is shown for creating a liner component. Similar to the method of FIGS. 5A and 5B, a strip 82' may be provided from an endless band 52' (shown in FIGS. 4A and 4B). Rather than wrap the strip 82' around a mandrel 92 in a longitudinal configuration, the strip 82' may be wound helically around a mandrel 92, as shown in FIGS. 6A and 6B. In this embodiment, the width "w" of the strip 82' may not bear any particular relationship to the size of the mandrel 92, other than being narrower than the length of the mandrel 92 such that the strip 82' is wrapped one or more times around the mandrel 92. For example, the strip 82' may be wound around the mandrel 92 with a single rotation of three hundred sixty degrees (360°) or less, e.g., between one half and one full rotation, or may be wound multiple times around the mandrel 92. The strip 82' may be wound such that the longitudinal edges 86' of the strip 82' are disposed adjacent one another along adjacent windings without overlap. The edges 86' may contact one another, e.g., butt up against one another, as shown in FIG. 6C, or may be spaced slightly apart, if desired (not shown). Alternatively, the longitudinal edges 86' may overlap one another (not shown), and the material of the strip 86' may be reflowed during subsequent processing to provide a substantially uniform thickness wall liner, if desired. Optionally, the helically wound strip 82' (or any of the other strips described herein) may include a composite coated liner, e.g., as described elsewhere herein.

As shown in FIGS. 9A-9D, the helically wound strip 82' may be incorporated into a tubular device 102,' e.g., including a reinforcing layer 104 and an outer layer 106, similar to the embodiment of FIGS. 8A-8D. The resulting tubular device 102' may include a coated lumen 103' similar to the tubular device 102, except that the seam from the strip 82' extends helically down the length of the tubular device 102' rather than axially as in the device 102.

Turning to FIGS. 7A-7F, another embodiment of a method for making liner components is disclosed. As explained above, an endless band 52 may be created that includes a coating on at least one of the inner and outer surfaces, e.g., inner surface 48a. The endless band 52 may be cut or otherwise separated into a plurality of narrower endless bands 82, as shown in FIG. 7B. For example, as shown in FIG. 7A, an array of cutters 85 may be provided that are spaced apart from one another by a distance corresponding to the desired width of each of the narrower endless bands 82, as described elsewhere herein. Alternatively, the narrower endless bands 82 may be formed sequentially by passing the endless band 52 multiple times through a cutting device (not shown) that creates one or more narrower endless bands 82 at a time.

Figure 7C:
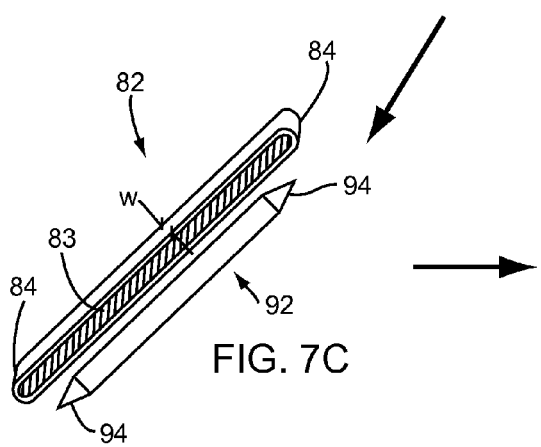
FIGS. 7C and 7D are perspective views of a narrow band being disposed around a mandrel.
Figure 7D:
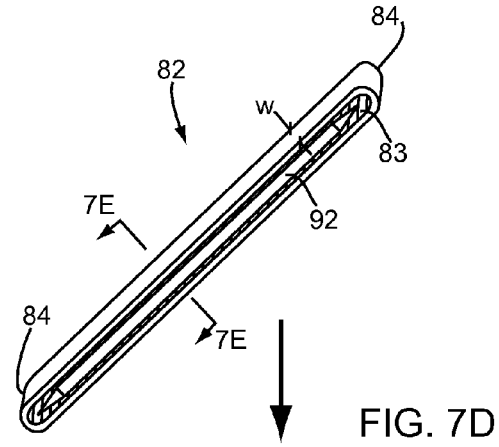
Figure 7E:
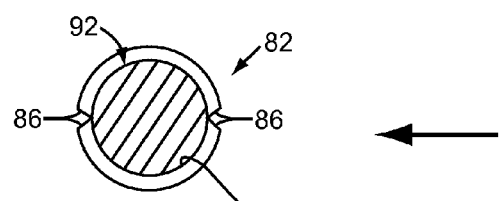
FIGS. 7E and 7F are cross-sectional details of the narrow band and mandrel of FIGS. 7C and 7D, showing the narrow band being disposed around the mandrel.
Figure 7F:
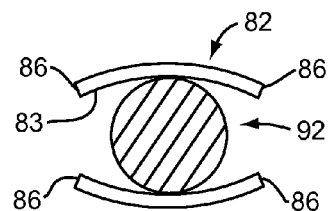

Each narrower endless band 82 may be wrapped around a mandrel 92 with the coated surface 83 oriented inwardly towards the mandrel 92. For example, as shown in FIGS. 7C and 7D, the narrower endless band 82 may be flattened and ends 84 of the band 82 may be received over respective ends 94 of the mandrel 92. The length of the flattened band 82 and the mandrel 92 may be such that the band 82 may be stretched slightly to receive the ends 84 over the ends 94 of the mandrel 92, e.g., to apply a slight tension along the length of the band 82. As shown in FIGS. 7E and 7F, the band 82 may wrap around the mandrel 92 such that longitudinal edges 86 of the band 82 are disposed adjacent one another and extend substantially axially between the ends 94 of the mandrel 92. Alternatively, if desired, the ends 84 of the band 82 may be rotated about the longitudinal axis of the mandrel 92 relative to one another, e.g., such that the longitudinal edges 86 of the band 82 extend helically between the ends 94 of the mandrel 92 (not shown).

Each narrower endless band 82 may have a width having a desired relationship with a circumference of a liner to be formed using the narrower endless band 82. More particularly, the width of the narrower endless band 82 may be substantially half or slightly less than half the circumference of mandrel 92. Thus, as shown in FIG. 7F, the inner most corners of the longitudinal edges 86 may contact one another or may be spaced slightly apart from one another (not shown), while the outer most corners of the longitudinal edges 86 are spaced apart from one another. Thus, the narrower endless band 82 may be wrapped around the mandrel 92 without the longitudinal edges 86 overlapping.

Alternatively, the width "w" of the narrower endless band 82 may be slightly smaller than half the circumference of the mandrel 92 such that a narrow gap (not shown) remains between the longitudinal edges 86 after wrapping the narrower endless band 82 around the mandrel 92. Such a gap may reduce the likelihood of the edges 86 of the narrower endless band 82 shifting and overlapping. In a further alternative, the longitudinal edges 86 may overlap, and the material of the band 86 may be reflowed during subsequent processing to provide a substantially uniform thickness wall liner, if desired (not shown).

Alternatively, multiple narrower endless bands (not shown) may be wrapped around the mandrel 92. The width "w" of each narrower endless band may be substantially equal to c/2n, where "c" is the circumference of the mandrel 92 and n is the number of narrower endless bands used. Alternatively, the width "w" of each of the multiple narrower endless bands (not shown) may be greater than or less than c/2n, resulting in overlaps or narrow gaps, respectively, similar to other embodiments described elsewhere herein.

Optionally, the ends 84 of the narrower endless band 82 may be rotated relative to one another, e.g., to wind the band 82 helically around the mandrel 92. In this option, the longitudinal edges 86 may provide a gap, may be butted together, or may be spaced apart, similar to other embodiments described elsewhere herein.

Turning to FIGS. 10A-10D, the narrower endless band 82, wrapped around the mandrel 92, may be incorporated into a tubular device 102," e.g., including a reinforcing layer 104 and an outer layer 106, similar to the embodiments of FIGS. 8A-9D. Optionally, after applying a reinforcing layer 104 and/or outer layer 106 around the narrower endless band 82 wrapped around the mandrel 92, the ends of the tubular device 102" may be trimmed or otherwise cut to length (not shown), as desired. The resulting tubular device 102" may include a coated lumen 103" similar to the tubular devices 102, 102,' except that the band 82 creates a pair of longitudinal seams that extend down the length of the tubular device 102." The longitudinal seams may extend axially or helically depending upon whether the ends 84 of the band 82 are rotated relative to one another or not.

Figure 11A:
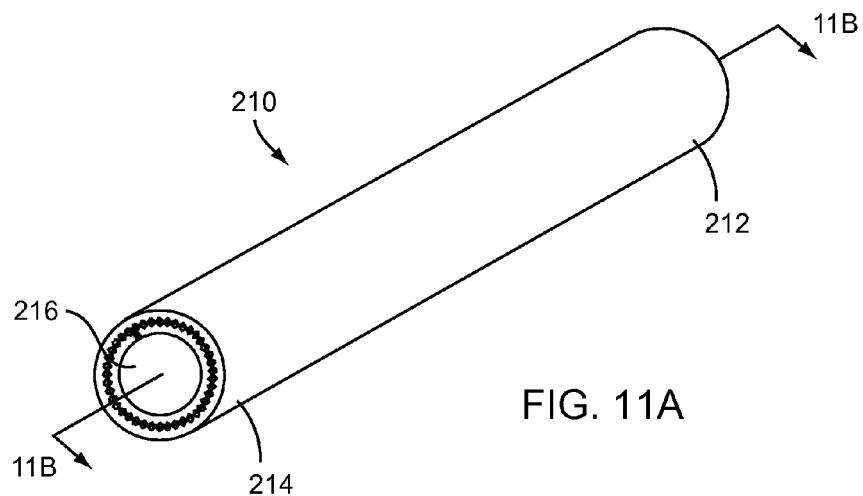
FIG. 11A is a perspective view of another exemplary embodiment of a tubular device, including a lumen extending between proximal and distal ends thereof.
Figure 11B:
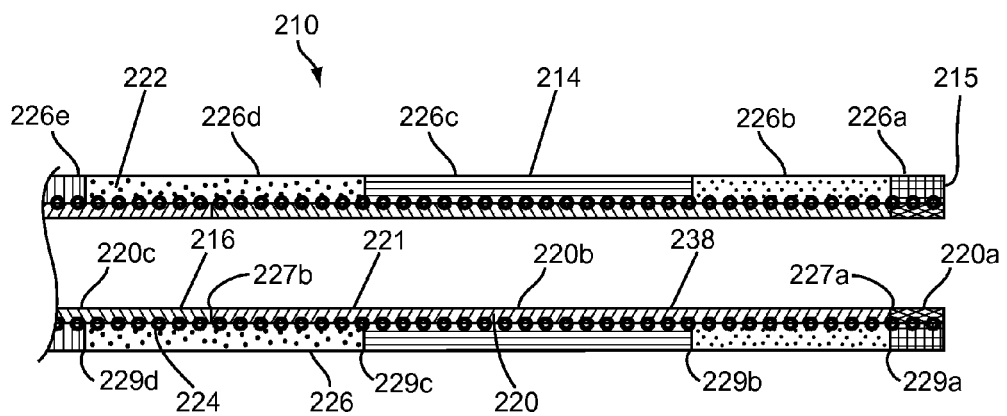
FIG. 11B is a cross-sectional view of the tubular device of FIG. 11A, taken along line 11B-11B, showing a coated liner surrounding the lumen having variable properties along a length of the tubular device.

Turning now to FIGS. 11A and 11B, another embodiment of a tubular device 210 is shown that may be made using the apparatus and methods described herein. Generally, the tubular device 210 is an elongate tubular member including a proximal end 212, a distal end 214 sized for insertion into a body lumen, and a lumen 216 extending between the proximal and distal ends 212, 214. The distal end 214 may terminate in a relatively soft and/or substantially atraumatic distal tip 215, as described further below. Optionally, the apparatus 210 may include one or more additional lumens, a handle and/or one or more ports, or other elements (not shown), similar to other embodiments described herein.

With particular reference to FIG. 11B, the apparatus 210 generally includes an inner liner 220 surrounding the lumen 216 and an outer layer 222 surrounding the inner liner 220, e.g., including a reinforcing layer 224 and an outer tubular layer 226. Similar to the previous embodiments, the inner liner 220 may include a relatively thin film, sheet, or other material including an inner surface 221, and the inner surface 221 may include a coating 238 having one or more desired properties, e.g., a hydrophilic coating.

Unlike the previous embodiments, the inner liner 220 may have a composite construction, e.g., formed from one or more sections of material 220a-220c having different properties than one another. In addition, the outer tubular layer 226 may also be formed from one or more sections of material 226a-226e, also having different properties than one another. Optionally, one or more of the seams 227a, 227b between the adjacent sections 220a-220c of the inner liner 220 may be offset axially from one or more of the seams 229a-229d between adjacent sections 226a-226e of the outer tubular layer 226.

For example, as shown in FIG. 1B, the distal tip 215 of the tubular device 210 may include a relatively soft material for both the outer tubular layer 226 and the inner liner 220, and the reinforcing layer 224 may terminate before the distal tip 215. In an exemplary embodiment, the inner liner 220 may include a distal-most section 220a formed from a relatively soft material, e.g., forty Durometer (40 D) polyurethane, and a distal-most section 226a of the outer tubular layer 226 may be formed from a relatively soft material, e.g., a thirty five Durometer (35 D) PEBAX, which optionally may be doped with Tungsten or Barium.

The distal tip 215 including sections 220a, 226a may be formed separately from the rest of the tubular device 210, e.g., using a lay-up process in which a tube (corresponding to section 226a of the outer tubular layer 226) may be lined with a thin sheet (corresponding to section 220a of the inner liner 220) and then separated into multiple lengths that provide tips for multiple devices. Additional information on methods for making such tips are disclosed in the applications incorporated by reference elsewhere herein.

Adjacent the distal tip 215, the inner liner 220 may include a transition section 220b, e.g., formed from fifty five Durometer (55 D) polyurethane or other material more rigid than the distal-most section 220a, and then a shaft section 220c, e.g., formed from seventy two Durometer (72 D) PEBAX or other material more rigid than the more distal transition section 220b, which may extend from the distal end 214 of the tubular device 210 to the proximal end 212. Similarly, the outer tubular layer 226 may include one or more transition sections 226b-226d (three shown) and a shaft section 226e, which may extend proximally towards the proximal end 212 of the tubular device 210. In the embodiment shown, the seams 229-229d of the outer tubular layer 226 are offset axially or staggered from the seam 227b of the inner liner 220, which may provide smoother stiffness transitions along the length of the distal end 214. Such smoother transitions may reduce the risk of the distal end 214 buckling or kinking, e.g., when the tubular device 210 is directed through tortuous anatomy.

In an exemplary embodiment, the transition sections 226b-226d of the outer tubular liner 226 may be formed from progressively more rigid material in sections away from the distal tip 215. For example, the first transition section 226b may be formed from forty Durometer (40 D) PEBAX, which optionally may be doped similar to the distal-most section 226a, the second transition section 226c may be formed from fifty five Durometer (55 D) PEBAX, and the third transition section 226d may be formed from sixty three Durometer (63 D) PEBAX. The shaft section 226e may be formed from nylon or Pebax, or other material, similar to the exemplary embodiments described elsewhere herein.

The tubular device 210 may be incorporated into a variety of catheters, sheaths, or other medical devices. In an exemplary embodiment, the tubular device 210 may be incorporated into a catheter for delivering cardiac leads into a patient's heart (not shown). In such an example, the tubular device 210 may have a length between about thirty and sixty five centimeters (30-65 cm), and an outer diameter between about four and ten French (4-10 Fr). The proximal end 212 of the tubular device 210 may include a handle or hub (not shown), which may include a port communicating with the lumen 216, e.g., including a hemostatic valve (also not shown), which may provide a substantially fluid-tight seal, while accommodating insertion of leads or other instruments or fluids into the lumen 216. Optionally, the distal end 214 of the tubular device 210 may be shape set in a desired configuration, e.g., biased to a simple or complex curved shape, e.g., as disclosed in the applications incorporated by reference elsewhere herein.

Figure 12E:
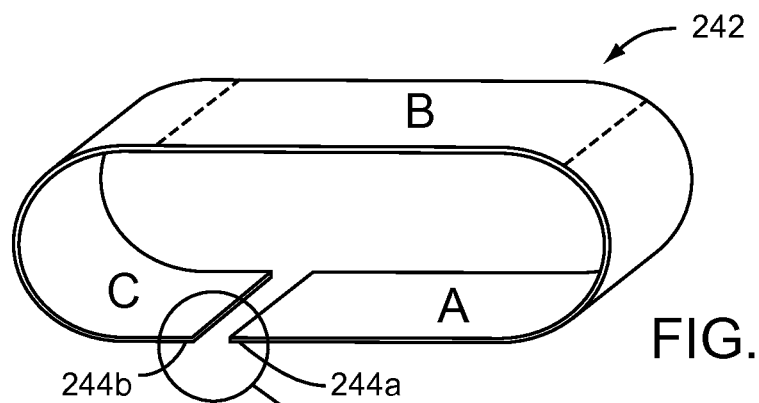
FIGS. 12E and 12F are perspective views of the composite sheet of FIG. 12D being rolled and having its ends attached together.

Turning to FIGS. 12A-12H, an exemplary method is shown for making composite coated liners for tubular devices, such as tubular device 210. As shown in FIG. 12A, a plurality of different materials may be provided, e.g., material A, material B, and material C, which may be cut into sheets that may be attached together to provide a composite sheet 242, as shown in FIG. 12D. For example, materials A, B, C may be cut or otherwise separated into individual sheets 242a, 242b, 242c having desired lengths, e.g., corresponding to the length of respective sections of one or more liners to be formed from the composite sheet 242. The sheets 242a, 242b, 242c may have widths corresponding to the width of an individual liner component or to multiple liner components, similar to the previous embodiments.

Adjacent edges of the sheets 242a, 242b, 242c may be attached together at seams 243a, 243b. For example, as shown in FIG. 12B, one or more heating assemblies 254 may be provided for simultaneously or sequentially fusing butted edges of the sheets 242a, 242b, 242c. Alternatively, as shown in FIG. 12C, edges of the sheets 242a, 242b, 242c may be lapped over one another by a desired distance and attached together, e.g., using the heating assembly 254. In either option, the resulting seams 243a, 243b may have a substantially uniform thickness, similar to the rest of the sheets 242a, 242b, 242c. Thus, the resulting composite sheet 242 may have a substantially uniform thickness and/or other substantially homogeneous mechanical properties. Alternatively, the thickness of the seams 243a, 243b may be greater or otherwise not the same as the rest of the composite sheet 242, e.g., if the seams 243a, 243b are reflowed during subsequent processing, similar to previous embodiments.

Figure 12G:
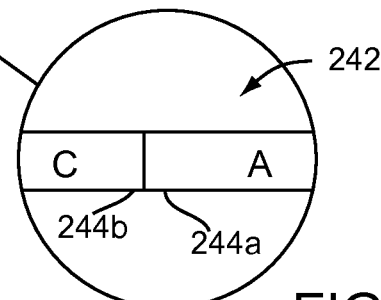
FIG. 12G is a detail showing the ends of the composite sheet of FIGS. 12E and 12F attached together to provide an endless band.
Figure 12H:
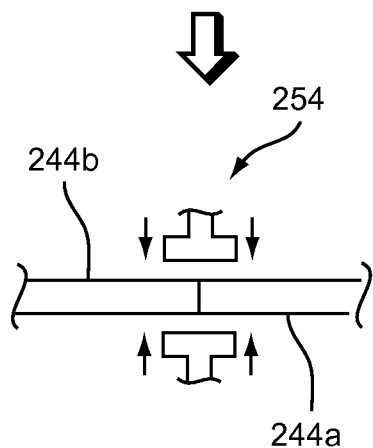
FIG. 12H is a detail showing a method for attaching the ends of the composite sheet of FIGS. 12E and 12F together to form a composite band in preparation for coating a surface of the composite sheet.

Turning to FIGS. 12E-12H, the composite sheet 242 may then be formed into an endless band 252, similar to the previous embodiments. As shown in FIGS. 12G and 12H, ends 244a, 244b of the composite sheet 242 may be attached together, e.g., using heating assembly 254. For example, the ends 244a, 244b may be butted together and attached, for example, by welding (e.g., sonic welding), fusing (e.g., heating, melting, or otherwise reflowing the material), bonding with adhesive, and the like. Alternatively, the ends 244a, 244b may be attached together using one or more fasteners (not shown), similar to previous embodiments, which may facilitate separating the ends 244a, 244b of the composite sheet 242 after processing the endless band 252, if desired.

Figure 15A:
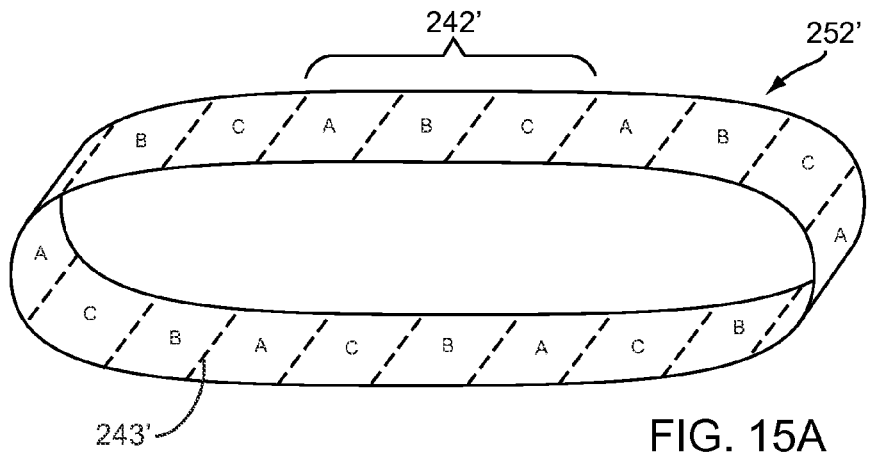
FIG. 15A is a perspective view of an alternative embodiment of a composite band including alternating sections having different material properties with edges of adjacent sections attached by orthogonal transitions.

In an alternative embodiment, shown in FIG. 15A, an endless band 252' may be formed from multiple composite sheets 242.' For example, materials A, B, C may be cut into identical sheets 242a,' 242b,' 242c' whose edges may be attached together in an alternating or sequential pattern. Thus, the sheets from each material may have the same length and width, although the lengths of the different material sheets may be different, similar to the previous embodiment. The resulting endless band 252' may be used to make multiple liner components, e.g., with the endless band 252' having a width corresponding to the individual liner components or multiple liner components.

Figure 15B:
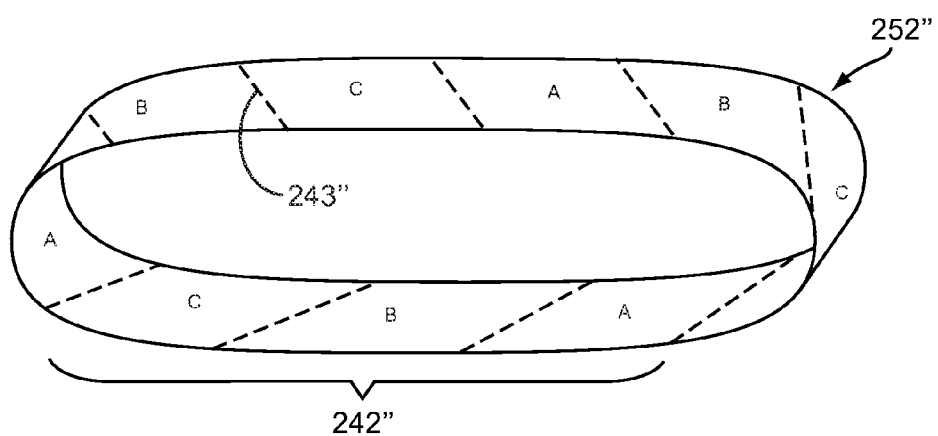
FIG. 15B is a perspective view of another alternative embodiment of a composite band including alternating sections having different material properties with edges of adjacent sections attached by non-orthogonal transitions.
Figure 15C:
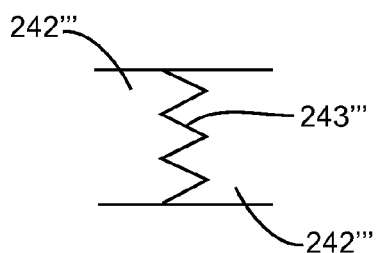
FIG. 15C is a top view of another alternative embodiment of a saw tooth seam that may be provided in a composite sheet.
Figure 15D:
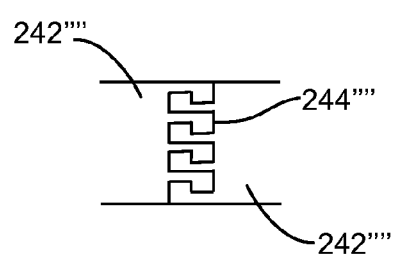
FIG. 15D is a top view of yet another alternative embodiment of an interlocked seam that may be provided in a composite sheet.

In the embodiment shown in FIG. 15A, the seams 243' between the adjacent sheets 242' may be substantially orthogonal, e.g., perpendicular, to the longitudinal edges of the endless band 252.' Alternatively, as shown in FIG. 15B, an endless band 252" may be provided that includes multiple sheets 242" whose adjacent edges are attached to define non-orthogonal seams 243." For example, the seams 243" may extend laterally relative to the longitudinal edges of the endless band 252." Turning to FIG. 15C, another alternative embodiment of a seam 243''' is shown that includes a saw tooth shape, e.g., by interlocking saw tooth edges of the adjacent sheets 242.''' Finally, FIG. 15D, shows yet another alternative embodiment of an interlocked seam 243''' that may be provided, if desired. Such non-orthogonal and/or interlocked seams may provide smoother transitions between dissimilar materials that an orthogonal seam.

Figure 13A:
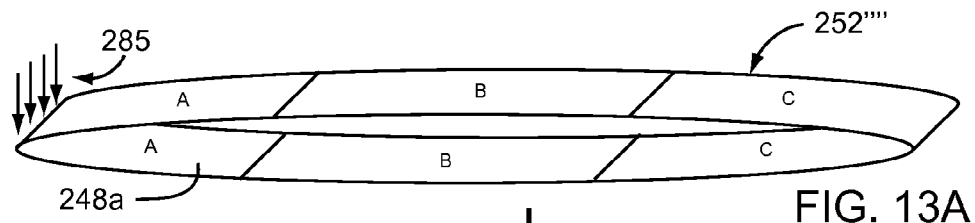
FIGS. 13A and 13B are perspective views of a composite band, e.g., formed from two sheets, such as that shown in FIG. 12D, and having a coated surface, being separated into separate relatively narrow composite bands.
Figure 13B:
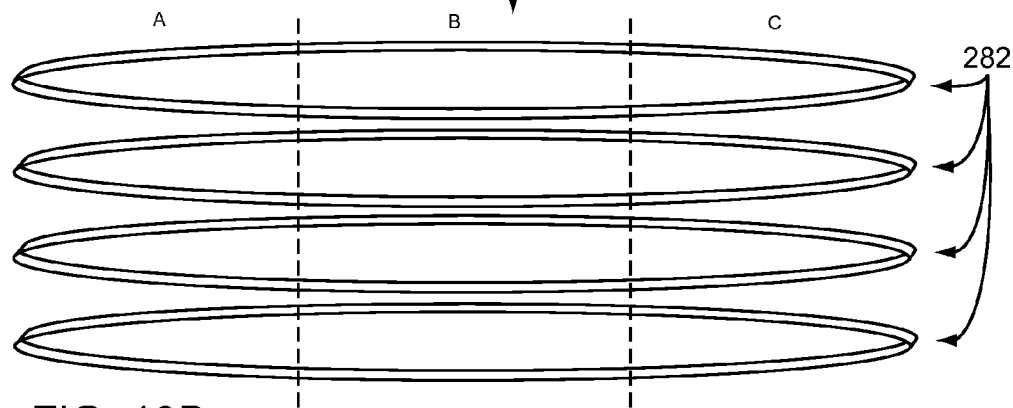

Returning to FIGS. 13A-13E, any of these composite endless bands may then be coated using any of the apparatus and methods described elsewhere herein with respect to other embodiments. For example, FIG. 13A shows an exemplary endless band 252'''' that has had a coating applied to its inner surface 248a. Similar to previous embodiments, the endless band 252'''' may be cut or otherwise separated into a plurality of relatively narrower endless bands 282, as shown in FIG. 13B, e.g., using cutting assembly 285 shown in FIG. 13A.

Figure 13C:
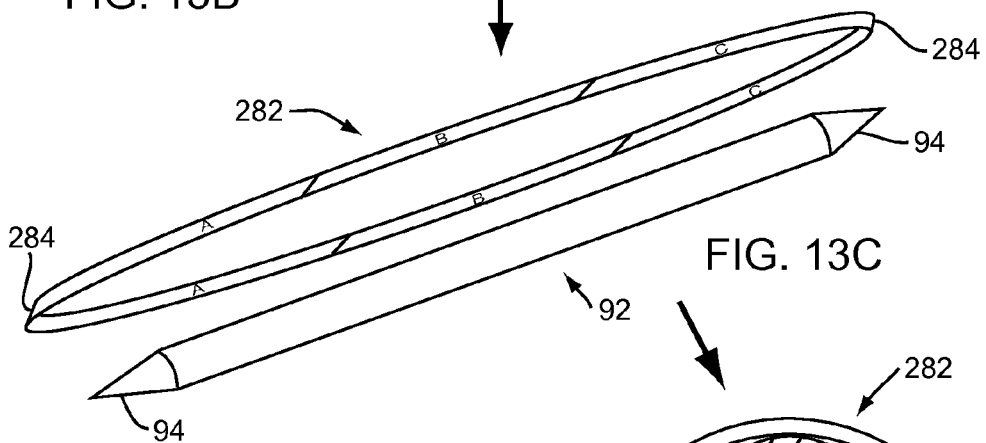
FIGS. 13C and 13D are perspective and cross-sectional views, respectively, of a relatively narrow composite band, such as those shown in FIG. 13B, being wrapped around a mandrel in a longitudinal configuration with the coated surface oriented inwardly towards the mandrel.
Figure 13D:
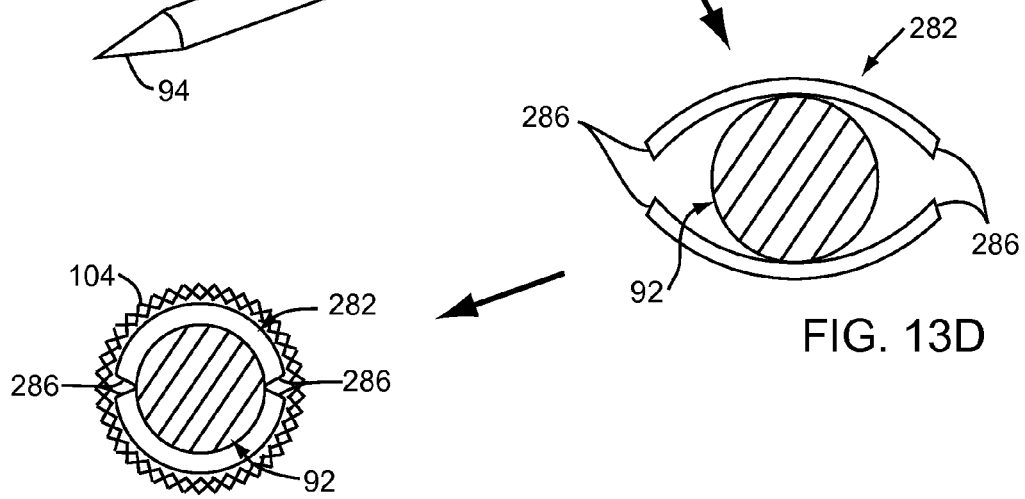
Figure 13E:
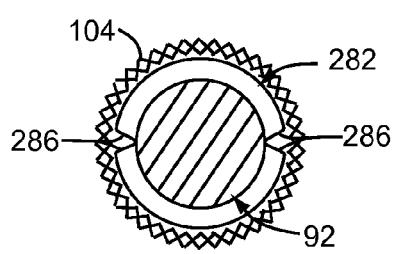
FIG. 13E is a cross-sectional view of the band and mandrel of FIGS. 13C and 13D with a reinforcing layer provided around the band.

Turning to FIGS. 13C-13E, each of the narrower endless bands 282 may be incorporated into a tubular device, similar to the previous embodiments. For example, as shown in FIG. 13C, a narrower endless band 282 may be flattened and ends 284 of the narrower endless band 282 may be received over respective ends 94 of the mandrel 92. In this embodiment, the sheets of the endless band 252'''' may be configured to ensure that the sections of the narrower endless bands 282 are symmetrical between ends 284. For example, if the intended liner includes three sections from materials A, B, C, the endless band 252'''' should include two sheets of each of these materials oriented opposite one another when the narrower endless band 282 is flattened, as shown in FIGS. 13A and 13B. As explained elsewhere herein, the sheets of the endless band 252'''' may be formed from different colors, which may facilitate identifying the transitions between the materials to confirm proper orientation of the narrower endless band 282 before being wrapped around the mandrel 92.

With particular reference to FIG. 13C, similar to the previous embodiments, the length of the flattened band 282 and the mandrel 92 may be such that the flattened band 282 may be stretched slightly to receive the ends 284 over the ends 94 of the mandrel 92, e.g., to apply a slight tension along the length of the endless band 82. As shown in FIGS. 13D and 13E, the endless band 282 may wrap around the mandrel 92 such that longitudinal edges 286 of the band 282 are disposed adjacent one another and extend substantially axially between the ends 94 of the mandrel 92. Alternatively, if desired, the ends 284 of the endless band 282 may be rotated about the longitudinal axis of the mandrel 92 relative to one another, e.g., such that the longitudinal edges 286 of the band 282 extend helically between the ends 94 of the mandrel 92 (not shown), similar to the previous embodiments.

Each narrower endless band 282 may have a width substantially half or slightly less than half the circumference of mandrel 92. Thus, the narrower endless band 282 may be wrapped around the mandrel 92 without the longitudinal edges 286 overlapping, similar to previous embodiments. Alternatively, the width "w" of the narrower endless band 282 may be slightly smaller than half the circumference of the mandrel 92 such that a narrow gap (not shown) remains between the longitudinal edges 286 after wrapping the narrower endless band 282 around the mandrel 92 or the longitudinal edges 286 (not shown), also similar to the previous embodiments.

Turning to FIG. 13E, the narrower endless band 282, wrapped around the mandrel 92, may be incorporated into a tubular device, e.g., including a reinforcing layer 104 and an outer layer (not shown), similar to the previous embodiments.

Figure 12F:
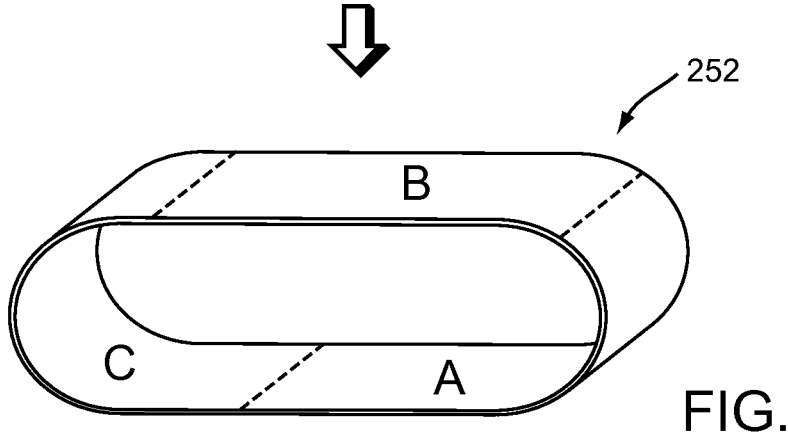
Figure 14A:
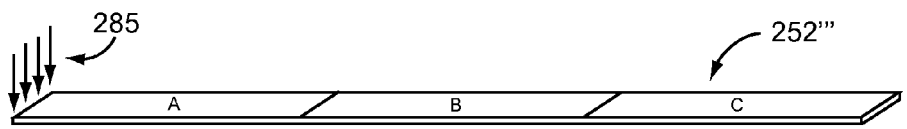
FIGS. 14A and 14B are perspective views of a composite sheet, such as that shown in FIG. 12D, being separated into separate composite strips after having a surface of the sheet coated.
Figure 14B:
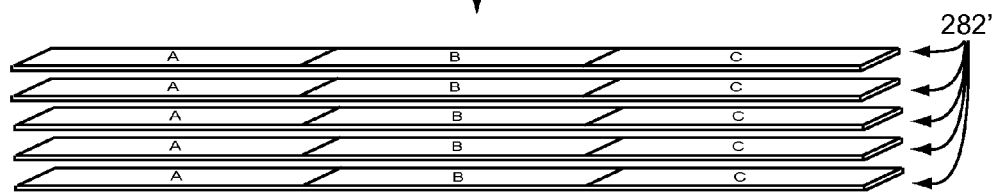

Turning to FIGS. 14A-14E, another exemplary method is shown for creating a plurality of liner components and/or tubular devices using the endless band 252 of FIG. 12F. In FIG. 14A, the endless band 252 has been cut or otherwise separated to provide a composite coated sheet 252.''' Using the cutting assembly 285, the composite coated sheet 252''' may be cut or otherwise separated into a plurality of strips 282,' e.g., as shown in FIG. 14B, which may be formed into individual liner components. If a coated endless band is created that includes multiple sequences of sheets, such as the endless band 252,' the individual sections 242' may be separated either after cutting the endless band 252' into narrower bands or after cutting across the endless band 252' to create a composite sheet (not shown), similar to FIG. 14A.

Figure 14C:
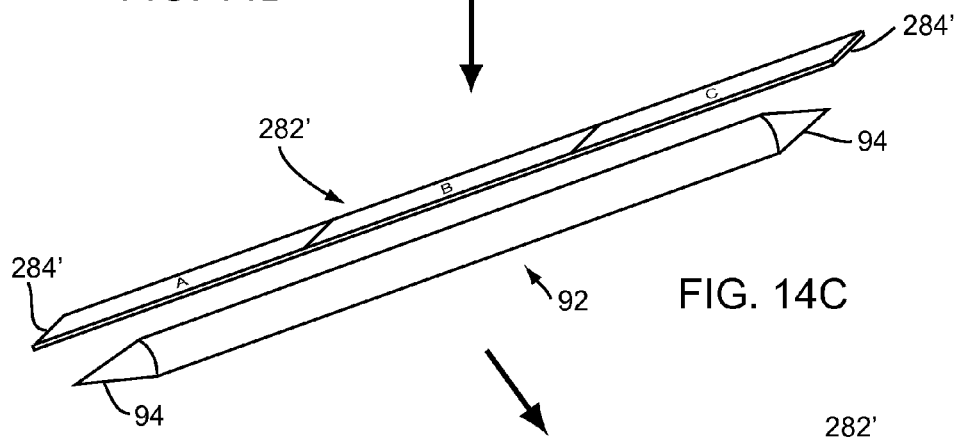
FIGS. 14C and 14D are perspective and cross-sectional views, respectively, of a composite strip, such as that shown in FIG. 14B, being wrapped around a mandrel in a longitudinal configuration with the coated surface oriented inwardly towards the mandrel.
Figure 14D:
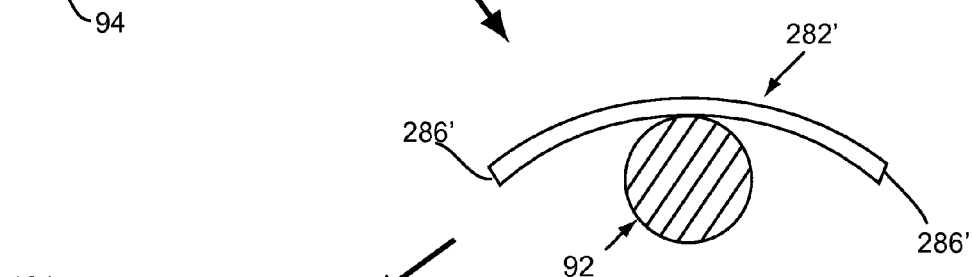
Figure 14E:
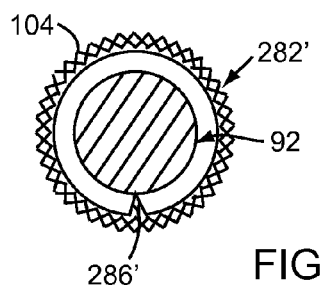
FIG. 14E is a cross-sectional view of the band and mandrel of FIGS. 14C and 14D with a reinforcing layer provided around the band.

Turning to FIGS. 14C-14E, each of the strips 282' may then be wrapped around a mandrel 92, e.g., until the longitudinal edges 286' of the strip 282' are disposed adjacent one another. For example, as shown in FIG. 14E, the inner most corners of the longitudinal edges 286' may contact one another or may be spaced slightly apart from one another (not shown), while the outer most corners of the longitudinal edges 86' are spaced apart from one another. Thus, the strip 282' may be wrapped around the mandrel 92 without the longitudinal edges 286' overlapping. Alternatively, the longitudinal edges 286' may be overlapped, if desired, similar to other embodiments herein.

Optionally, the ends 284' of the strip 282' may be secured relative to the mandrel 92, for example, by hooking the ends 284, around the ends 94 of the mandrel 92, e.g., stretching the strip 282' to apply a slight tension along the length of the strip 282.' The strip 282' wrapped around the mandrel 92 may be incorporated into a tubular device, e.g., including a reinforcing layer 104 and an outer layer (not shown), similar to the previous embodiments.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for making a tubular device sized for introduction into a body lumen, comprising:
   mounting an endless band to an apparatus that moves the band along an enclosed path including one or more coating elements;
   applying a coating to at least one of the inner surface and the outer surface using the one or more coating elements;
   separating the endless band into a plurality of narrower endless bands after applying the coating;
   positioning one of the narrower bands over opposite ends of an elongate mandrel such that the coating is disposed inwardly towards the mandrel and the narrower endless band wraps partially around the mandrel such that longitudinal edges of the narrower endless band extend between the opposite ends of the mandrel; and
   attaching a tubular structure around the narrower endless band while wrapped around the mandrel.

2. The method of claim 1, wherein the endless band comprises a plurality of sections of material having different material properties attached together in an alternating sequence to provide a composite endless band.

3. A method for making a tubular device sized for introduction into a body lumen, comprising:
   providing a sheet of material having first and second ends and longitudinal edges extending between the first and second ends, the sheet having a width between the longitudinal edges that is substantially smaller than a length of the sheet between the first and second ends;
   attaching the first and second ends of the sheet together to create an endless band including an inner surface and an outer surface;
   mounting the endless band to an apparatus that moves the band along an enclosed path including one or more coating elements;
   applying a coating to at least one of the inner surface and the outer surface using the one or more coating elements;
   separating the endless band into one or more strips after applying the coating;
   wrapping a strip from the one or more strips around a mandrel such that the coating is disposed inwardly towards the mandrel; and
   attaching a tubular structure around the wrapped strip and mandrel.

4. The method of claim 3, wherein the one or more coating elements comprise at least one of a sprayer, a roller, a brush, and a dipping assembly for applying coating material to the at least one of the inner surface and the outer surface of the endless band.

5. The method of claim 4, wherein the one or more coating elements further comprise a curing device that cures the coating material applied to the at least one of the inner surface and the outer surface of the endless band.

6. The method of claim 3, wherein wrapping a strip from the one or more strips around a mandrel comprises securing ends of the strip to ends of the mandrel, and wrapping longitudinal edges of the strip at least partially around the mandrel in a longitudinal configuration.

7. The method of claim 3, wherein wrapping a strip from the one or more strips around a mandrel comprises wrapping the strip helically around the mandrel between first and second ends of the mandrel.

8. The method of claim 3, wherein providing a sheet of material comprises attaching sections of material having different material properties together in an alternating sequence extending between the first and second ends.

9. The method of claim 8, wherein adjacent edges of the sections of material are attached together in an orthogonal configuration.

10. The method of claim 3, wherein separating the endless band into one or more strips comprises:
    cutting the endless band between the longitudinal edges to provide one or more coated sheets, each coated sheet having a length and a width; and
    cutting the coated sheet into a plurality of strips, each strip having a width smaller than the width of the coated sheet.

11. The method of claim 10, wherein the length of each strip is substantially the same as a length of the sheet of material between the first and second ends.

12. The method of claim 3, wherein wrapping the strip around a mandrel and attaching a tubular structure around the wrapped strip and mandrel are completed using a substantially continuous process.

13. A method for making a tubular device sized for introduction into a body lumen, comprising:
    providing an endless band having longitudinal edges, the endless band having a width between the longitudinal edges that is substantially smaller than a length around a periphery of the endless band;
    mounting the endless band to an apparatus that moves the band along an enclosed path including one or more coating elements;
    applying a coating to at least one of an inner surface and an outer surface of the endless band using the one or more coating elements;
    separating the endless band into one or more liner components after applying the coating;
    wrapping one or more liner components around a mandrel such that the coating is disposed inwardly towards the mandrel; and
    attaching a tubular structure around the wrapped liner component and mandrel.

14. A method for making a tubular device sized for introduction into a body lumen, comprising:
    providing an endless band having longitudinal edges;
    mounting the endless band to an apparatus that moves the endless band along an enclosed path including one or more coating elements;
    applying a coating to at least one of an inner surface and an outer surface of the endless band using the one or more coating elements;
    separating the endless band into a plurality of narrower bands after applying the coating, each narrower band having a width between the longitudinal edges that is substantially smaller than a length around a periphery of the narrower band;
    wrapping a band from the plurality of narrower bands around a mandrel such that the coating is disposed inwardly towards the mandrel and longitudinal edges of the band extend between ends of the mandrel; and
    attaching a tubular structure around the wrapped band and mandrel.

15. The method of claim 3, wherein the endless band is moved along the enclosed path once to apply the coating.

16. The method of claim 3, wherein the endless band is moved along the enclosed path more than once to apply the coating.

* * * * *